(12) United States Patent
Lelievre et al.

(10) Patent No.: US 12,340,876 B2
(45) Date of Patent: *Jun. 24, 2025

(54) METHOD RELATED TO ORGANIC COMPOSITIONS

(71) Applicant: GIVAUDAN SA, Vernier (CH)

(72) Inventors: Dominique Lelievre, Kindhausen (CH); Calice Becker, Paris (FR); Andreas Muheim, Waedenswil (CH)

(73) Assignee: GIVAUDAN SA, Vernier (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/647,979

(22) Filed: Apr. 26, 2024

(65) Prior Publication Data

US 2024/0312573 A1    Sep. 19, 2024

Related U.S. Application Data

(63) Continuation of application No. 17/055,461, filed as application No. PCT/EP2019/065216 on Jun. 11, 2019, now Pat. No. 12,002,550.

(30) Foreign Application Priority Data

Jun. 11, 2018 (GB) ..................................... 1809528

(51) Int. Cl.
   *G16C 20/30*   (2019.01)
   *C11B 9/00*   (2006.01)
   (Continued)

(52) U.S. Cl.
   CPC ............. *G16C 20/30* (2019.02); *C11B 9/00* (2013.01); *G06F 3/0488* (2013.01); *G06N 5/04* (2013.01);
   (Continued)

(58) Field of Classification Search
   None
   See application file for complete search history.

(56) References Cited

U.S. PATENT DOCUMENTS 5,508,259 A *  4/1996  Holzner ............... A61Q 13/00
                                                    424/65
7,030,079 B1 *  4/2006  Apel .................... A61K 8/4926
                                                    512/1

(Continued)

FOREIGN PATENT DOCUMENTS

WO   2008090397 A1   7/2008
WO   2018050721 A1   3/2018

OTHER PUBLICATIONS

International Search Report for corresponding application PCT/EP2019/065216 dated Jul. 11, 2019.
(Continued)

*Primary Examiner* — Lina Cordero
(74) *Attorney, Agent, or Firm* — Norris McLaughlin, PA

(57) ABSTRACT

Computer-implemented methods predict the temporal profile of at least one composition comprising a plurality of fragrance ingredients which are able to provide, fragrance, odor, or smell. The methods comprise using a processor to: retrieve a diffusion measure of how fast each fragrance ingredient diffuses into a headspace; form groups of fragrance ingredients having the same or a similar diffusion measure; determine the olfactive contribution of each fragrance ingredient; calculate the total olfactive contribution of a group of fragrance ingredients as the sum of the olfactive contributions of all fragrance ingredients forming said group; and provide a virtual olfactive fingerprint of the at least one composition based on the total olfactive contributions of the groups of fragrance ingredients and the diffusion measures of the groups of fragrance ingredients.

50 Claims, 12 Drawing Sheets

(51) Int. Cl.
  *G06F 3/0482* (2013.01)
  *G06F 3/0488* (2022.01)
  *G06N 5/04* (2023.01)
  *G06Q 10/101* (2023.01)
  *G16C 20/80* (2019.01)

(52) U.S. Cl.
  CPC ............ *G16C 20/80* (2019.02); *G06F 3/0482* (2013.01); *G06Q 10/101* (2013.01)

(56) References Cited

U.S. PATENT DOCUMENTS

| | | | | |
|---|---|---|---|---|
| 2005/0208673 | A1* | 9/2005 | Labreche | G01N 33/0034 422/98 |
| 2007/0042934 | A1* | 2/2007 | Fadel | A61K 8/18 512/1 |
| 2011/0015965 | A1* | 1/2011 | Morgan, III | G06Q 10/101 705/7.32 |
| 2011/0091404 | A1* | 4/2011 | Wohrle | A61K 8/37 512/17 |
| 2015/0275132 | A1 | 10/2015 | Denutte et al. | |
| 2017/0073614 | A1 | 3/2017 | Alchenberger et al. | |
| 2019/0218476 | A1* | 7/2019 | Blondeau | C11B 9/008 |
| 2020/0325415 | A1* | 10/2020 | O'Leary | C11B 9/00 |

OTHER PUBLICATIONS

GB Search Report for corresponding application GB 1809528.1 dated Dec. 4, 2018.

C. Vuilleumier, et al: "Multidimensional Visualization of Physical and Perceptual Data Leading to a Creative Approach in Fragrance Development"; Perfumer and Flavorist; vol. 33; pp. 54-61, Sep. 2008.

Written Opinion of the International Searching Authority for corresponding application PCT/EP2019/065216 dated Jul. 11, 2019.

* cited by examiner

| Formula sliced | Formula sliced Fragrance | VP Slice | Group code | Name | Concentration | Vapor Pressure | Threshold |
|---|---|---|---|---|---|---|---|
| Search columns | 56B | 4 | 4331001 | DAMASCONE... | 3 | 242.19 | 0.25 |
| NUMBERS | 56B | 3 | 6623501 | LINALOL SYNT | 30 | 1408.09 | 2.40 |
| Concentration | 56B | 3 | 9405101 | TRICYCLAL | 6 | 1926.19 | 3.29 |
| Concentration/Threshold | 56B | 3 | 0333001 | ACET HEXEN... | 3 | 8930.00 | 15.52 |
| Dilution factors | 56B | 3 | 5732451 | HEXENOL-3-CIS | 3 | 5211.00 | 13.31 |
| log(OV*concentration) | 56B | 3 | 4524001 | DIHYDROMY... | 50 | 1200.00 | 5.04 |
| log(OV)*concentration | 56B | 4 | 0176121 | ACET BENZYLE | 20 | 931.00 | 22.76 |
| Odor value | 56B | 3 | 7599001 | OENANTHAT... | 25 | 1345.00 | 82.06 |
| OV * concentration | 56B | 4 | 1032501 | AGRUMEX | 40 | 773.20 | 88.23 |
| Threshold | 56B | 6 | 0015333 | SERENOLIDE | 60 | 2.59 | 0.43 |
| Vapor Pressure | 56B | 6 | 9310001 | THIBETOLIDE | 40 | 6.64 | 1.42 |
| VP (100%) | 56B | 5 | 6186001 | ISOBUTYRAT... | 140 | 20.30 | 24.88 |
| VP Slice | 56B | 6 | 1320001 | ALD A HEXYL... | 50 | 3.72 | 9.68 |
| CATEGORIES | 56B | 5 | 4663501 | DIPROPYLEN... | 530 | 70.42 | 1732.98 |
| Fragrance | 56B | 1 | | | | | |
| Group code | 56B | 2 | | | | | |
| Name | 56B | 7 | | | | | |
| Odor Family | 56B | 8 | | | | | |
| 1 filter changed | | | | | | | |
| Fragrance (56B) | | | | | | | |

Fig. 14a

| Odor Value | Dilution factor | Odor family | VP(100%) | log(OV)*Co... | log(OV)*Co... | OV*Concent... | Concentratio... | Filters |
|---|---|---|---|---|---|---|---|---|
| | | | | | | | | Type to search filters |
| 959521.00 | | FRUITY | 242.19 | 6.45 | 17.95 | 2878863.00 | 11.89 | Group Code |
| 587273.00 | | FLORAL | 1408.09 | 7.25 | 173.07 | 1761819.00 | 12.51 | Type to search in list |
| 585468.00 | | GREEN | 1926.19 | 6.55 | 34.61 | 3512808.00 | 1.82 | All (14 values) / 0015333 / 0178121 / 033001 / 1532501 / 132001 / 4331001 |
| 575468.00 | | GREEN | 8930.80 | 6.24 | 17.28 | 1726398.00 | 0.19 | |
| 391561.00 | | GREEN | 5211.00 | 6.07 | 16.78 | 1174683.00 | 0.23 | |
| 238151.00 | | CITRUS | 1200.00 | 7.08 | 268.84 | 1190755.00 | 9.92 | Name |
| 40913.00 | | FRUITY | 931.00 | 5.91 | 92.24 | 818260.00 | 0.88 | Type to search in list |
| 16391.00 | | FRUITY | 1345.00 | 5.61 | 105.37 | 409775.00 | 0.30 | (All) 14 values / ACET BENZYLE / ACET HEXENYLE-3-CIS / AGRUMEX / ALD A HEXYL CINNAM... / DAMASCONE ALPHA / DAMASCONE DELTA |
| 8764.00 | | FRUITY | 773.20 | 5.54 | 157.71 | 350560.00 | 0.45 | |
| 6014.00 | | MUSK | 2.59 | 5.56 | 226.75 | 360840.00 | 139.21 | |
| 4682.00 | | MUSK | 6.64 | 5.27 | 146.82 | 187280.00 | 28.21 | Concentration |
| 816.00 | | FRUITY | 20.30 | 5.06 | 407.64 | 114240.00 | 5.63 | include empty values |
| 384.00 | | FLORAL | 3.72 | 4.28 | 129.22 | 19200.00 | 5.17 | Fragrance |
| 41.00 | | | 70.42 | 4.34 | 854.78 | 21730.00 | 0.31 | 56A / 56C / 56D / 56E |
| | | | | 0.00 | 0.00 | 0.00 | 0.00 | VP (100%) 0.09 — 5900 |
| | | | | 0.00 | 0.00 | 0.00 | 0.00 | include empty values |
| | | | | 0.00 | 0.00 | 0.00 | 0.00 | Vapor Pressure 0.09 — 59643 |
| | | | | 0.00 | 0.00 | 0.00 | 0.00 | include empty values |
| | | | | | | | | Threshold 0.01 — 17327.98 |
| | | | | | | | | include empty values |
| | | | | | | | | Odor Value 41.0 — 6286632 |
| | | | | | | | | include empty values |
| | | | | | | | | Dilution factor |
| | | | | | | | | 1 filter changed |

Fig. 14b

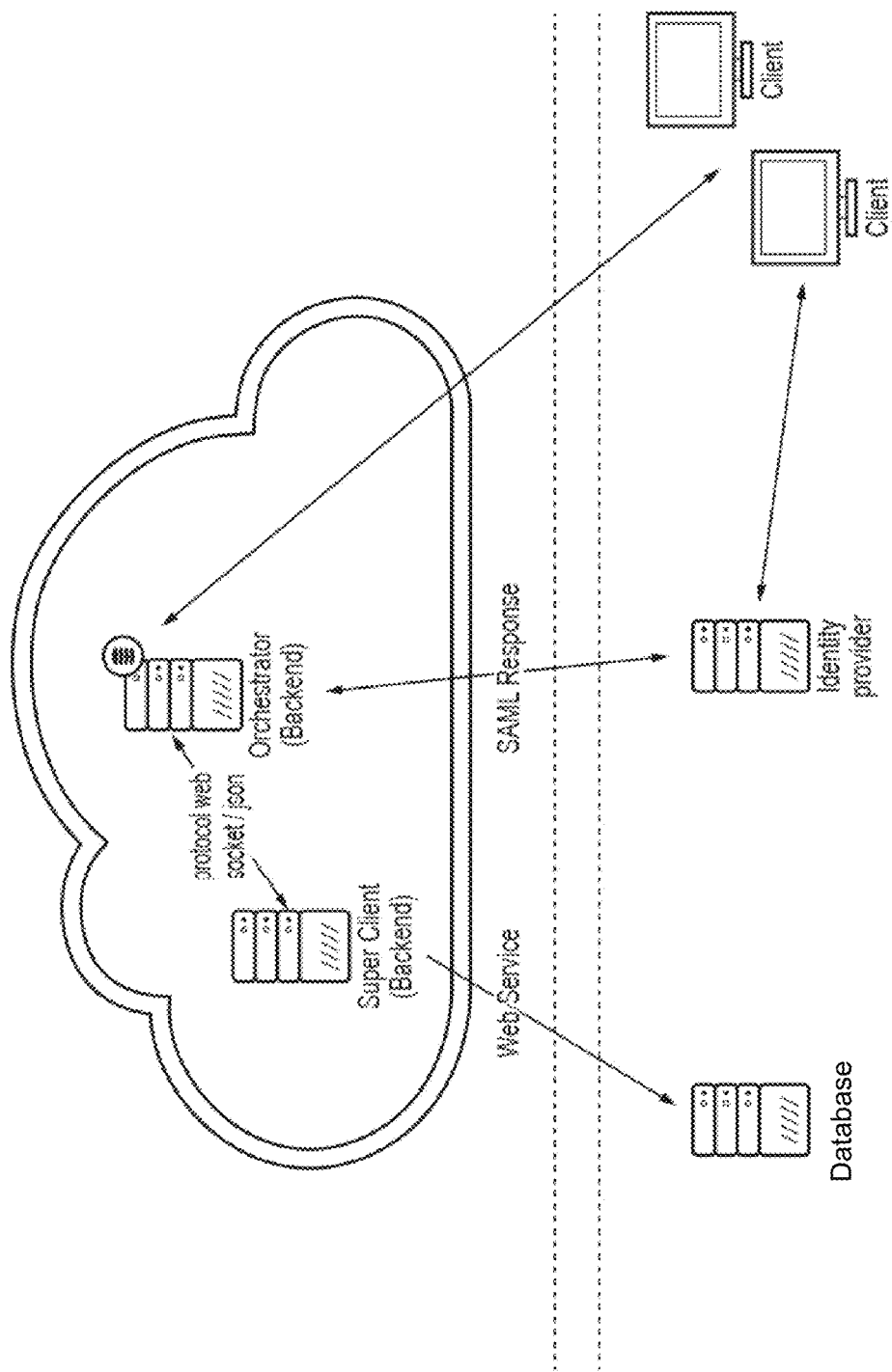

METHOD RELATED TO ORGANIC COMPOSITIONS

This application is continuation of U.S. patent application Ser. No. 17/055,461, filed 13, Nov. 2020, which is an application filed under 35 USC 371 of PCT/EP2019/065216, filed 11, Jun. 2019, which claims priority to GB 1809528.1, filed 11, Jun. 2018. The present application claims all priority benefits of the foregoing identified applications, as well as incorporating the entirety of their disclosures herein by reference thereto.

The present invention relates to a computer-implemented method of predicting the temporal fragrance profile of a fragrance composition comprising a plurality of fragrance ingredients, and to methods of adjusting or balancing the temporal fragrance profile of a fragrance composition, as well as to a computer program and an apparatus for carrying out said methods.

State of the art fragrance compositions are prepared using a palette of fragrance ingredients. At the heart of the fragrance creation process lies the skill the perfumer exercises in making inspired combinations from the ingredients palette. However, modern technologies are typically used to aid in the creative process. For example, the ingredients' palette is typically stored on a computer database, which allows recipes to be created and displayed on a computer user interface. The computer, in turn, may be in communication with a mixing robot.

A recipe will typically be displayed on a computer interface in the form of a list (in spreadsheet form) of the names of the selected ingredients, together with information related to the concentration of each ingredient. Based on the olfactive character of each of the selected ingredients, as well as the relative proportions in which they are employed, an experienced perfumer may be able to form a reasonable mental impression of the odor of the composition, which will be of some assistance in guiding him or her through the creation process. Once the recipe is finalized, a digital signal expressing the recipe can be sent to an output device, which is adapted to mix and dispense the fragrance composition for olfactive assessment. However, even for very experienced perfumers, the creative process can entail multiple iterations of recipe adjustment in which complex creations require multiple design, dispensing and olfactive assessment steps, all of which is time consuming, exhausting on the nose of the perfumer, and is wasteful of valuable perfume ingredients.

Moreover, the fragrance profile of a fragrance composition will generally vary over time due to volatility differences: Some fragrance ingredients will evaporate quickly and thus be perceived very early on, while other fragrance ingredients will evaporate slowly and may have a much more long-lasting effect. Optimizing the temporal fragrance profile of a fragrance composition is one very important aspect of the fragrance creation process, which requires the perfumer to assess the impact of the fragrance composition over an extended period of time, thus rendering the whole process even more time consuming.

However, in addition to these issues that are essentially associated with process efficiency, the creation process is also an important moment in the development of the relationship between the perfumer and the customer. Fragrance creations are critically important components of the identity of branded products, and it is important that they are favorably received by the customer. To this end, it is not uncommon for customers to be closely involved in the creation process, in the expectation of creating trust and understanding, which in turn can positively influence customer preference and acceptance. However, despite the attendant advantages of this co-creation approach, the nomenclature of classical odor description used by perfumers to communicate with clients is somewhat subjective and can in some cases create barriers to understanding and ultimately preference and acceptance. Moreover, the spreadsheet list of ingredients that the perfumers work with is impenetrable to a non-expert and "flat" even to experts.

There remains a need for a design aid that enables perfumers, evaluators and any other actors involved in the creation process to better understand and communicate the sensory and functional attributes of a perfume composition, rendering the design process simpler, faster, cheaper, and more sustainable, thereby promoting customer acceptance and preference for fragrance creations.

These needs are addressed by the present invention, which provides in a first aspect a computer-implemented method of predicting the temporal fragrance profile of a fragrance composition comprising a plurality of fragrance ingredients, the method comprising using a processor to: retrieve a diffusion measure of how fast each fragrance ingredient diffuses into a headspace; form groups of fragrance ingredients having the same or a similar diffusion measure; retrieve the olfactive contribution of each fragrance ingredient; calculate the total olfactive contribution of a group of fragrance ingredients as the sum of the olfactive contributions of all fragrance ingredients forming said group; and using a graphical user interface, GUI, to: display the total olfactive contribution of each group of fragrance ingredients in the order of their respective diffusion measures to visualize the temporal fragrance profile of the fragrance composition.

Advantageously, embodiments allow the temporal profile of a perfume to be viewed and possibly modified, without the iterative enhancements based on the perfumer's experience which are a feature of the current methodology. The improved visualization is a de-segmentation of the ingredients according to the grouping, fostering a better understanding of the composition's development over time.

In the context of the present invention, the term "temporal fragrance profile" is meant to include the temporal profile of both fragrance and flavor compositions. The latter typically also emanate an odor, which may be perceived ortho- and/or retro-nasally.

Alternatively or in addition, it is also possible to group the fragrance ingredients based on their odor value. In this embodiment, groups of fragrance ingredients having the same or a similar odor value, rather than diffusion measure, are formed. This kind of grouping allows for equalizing the fragrance profile over time-fragrance ingredients with the same or similar odor value can be used in similar amounts to provide the same or similar contribution, and will therefore evolve in a similar manner over time.

The odor value is determined by dividing the equilibrium headspace concentration of the fragrance ingredient by its odor threshold.

The odor threshold of a fragrance ingredient can be determined, for instance, by either one of the two following measurements:

a) Olfactometer Odor Threshold:
    Using an olfactometer, the following steps were carried out to determine the odor thresholds of the fragrance ingredient.
    The olfactometer functions on the principle of a linear dilution of a fragrance ingredient in a carrier gas. The quantity of fragrance ingredient displaced depends on its vapor pressure and the carrier gas flow. A constant flow of nitrogen, regulated by a flow regulator, carries the fragrance ingredient from a sample container to a mixing chamber. There, the carrier gas-odor mixture is diluted with odorless air. From the mixing chamber, one part of the diluted odorous air is allowed to flow via a fused silica capillary to the sniffing funnel. The flow rate through the capillary, which determines the dosage of odorous air from the mixing chamber into the sniffing funnel, depends on the opening of the valve, which can be regulated from 1 to 256 ml in binary steps. The final dilution of the odorous air sample occurs in the glass funnel by flushing permanently with odorless air at a flow rate of 8 l/min. Forced-choice triangle presentation is achieved by a special automated channel setting device where the fragrance ingredient delivering capillary enters in the sniffing funnel only in one position of a switch, whereas in two other positions the capillary is positioned outside the funnel and where the effluent is sucked away. After each trial, the channel setting is changed automatically and in a random order. The concentration is calculated from the fragrance ingredient's vapor pressure and from the dilution ratios that were applied in the olfactometer, assuming that vapor pressure saturation is achieved in the sample generator. As a control, the concentration is determined analytically by sampling a known volume from the capillary effluent into a headspace filter and by subsequent gas chromatographic quantitation of the fragrance ingredient in the desorption solution.

Each panelist (panel of 15 persons) starts sniffing at the olfactometer at a concentration level at which he perceives the fragrance ingredient at medium intensity. After three correct answers in three consecutive trials (or four correct ones of five trials) at the same level, stimulus concentration is decreased by a factor of two to the next lower level, and so on, until the panelist has reached his threshold level. The final threshold value of a given fragrance ingredient is obtained as the mean value of all individual threshold levels.

Further information of the technique hereinabove described may be found in chapter 6 of Neuner-Jehle, N. and Etzweiler, F., Perfumes: Art, Science and Technology; Müller, P.; Lamparsky, D., Eds; Elsevier Applied Science Publishers: London, 1991; pp 153-212.

b) GC Odor Threshold:

The odor threshold values were determined by gas chromatograph (GC) detection. Different dilutions of a tested fragrance ingredient were injected into a GC in descending order of concentration until a panelist failed to detect the respective substance at the sniffing port. Each panelist (panel of 5 persons) smelled blind and pressed a button upon perceiving an odor. If the recorded time matched the retention time, the sample was further diluted. The last quantity detected at the correct retention time is the individual odor threshold. The final threshold value of a given fragrance ingredient is obtained as the mean value of all individual threshold levels.

Further information of the technique hereinabove described may be found in chapter 6 of Neuner-Jehle, N. and Etzweiler, F., Perfumes: Art, Science and Technology; Müller, P.; Lamparsky, D., Eds; Elsevier Applied Science Publishers: London, 1991; pp 153-212.

The diffusion measure of how fast each fragrance ingredient diffuses into a headspace may be the equilibrium headspace concentration, or partial vapor pressure or vapor pressure, or retention time on a gas chromatograph, or vapor liquid equilibrium, VLE, or be based on the maximal abundance time where the abundance in a headspace reaches its maximum.

The equilibrium headspace concentration (HS) of a fragrance ingredient is one preferred measure of how fast a fragrance diffuses into a headspace (air surrounding an object) and is directly related to its partial vapor pressure p (pressure exerted by the individual fragrance in the mixture) through the law of perfect gases:

$$HS = \left(\frac{1000 * MW}{RT}\right) * p$$

wherein HS is the equilibrium headspace concentration given in µg/l headspace, MW is the molecular weight of the fragrance ingredient given in g/mol, R is the gas constant (R=8.314510 J·mol$^{-1}$K$^{-1}$), T is the absolute temperature given in Kelvin (T=298.15 K at 25° C.), p is the partial vapor pressure given in Pascal, and the pre-factor 1000 accounts for the transformation of liter headspace into cubic meter headspace and of grams to micrograms. The equilibrium headspace concentration is typically measured at 25° C. It will be appreciated that equilibrium headspace concentration increases with molecular weight and with vapor pressure.

Vapor pressure itself is another preferred diffusion measure.

A fragrance composition is a composition comprising one or more fragrance ingredients, which is able to provide a fragrance, odor or smell. The terms fragrance, odor and smell are used interchangeably throughout this description. Typical applications of fragrance compositions include, but are not limited to, personal care products, laundry care products, home care products, and air care products.

The first impression of a fragrance composition is typically dominated by its headspace, i.e. the volatile components emanating from the composition. Typically, the fragrance profile will then evolve and change over time, depending on the volatilities of the fragrance ingredients present.

A fragrance ingredient may be a single chemical substance or a combination of chemical substances. Furthermore, the fragrance ingredients may have natural, semi-synthetic or synthetic origin. It is also possible to use a sub-formula, i.e. a combination of fragrance ingredients that are used in a fixed ratio, and to add such a sub-formula as one ingredient. The fragrance ingredients may be selected from a database of fragrance ingredients. A comprehensive list of suitable ingredients may be found in the perfumery literature, for example "Perfume & Flavor Chemicals", S. Arctander (Allured Publishing, 1994), as well as later editions of this work, which are herein incorporated by reference.

The equilibrium headspace concentration of a fragrance ingredient can be determined, for instance, by the following measurement:

500 mg of the test fragrance ingredient was added to a headspace container which was then sealed. The container was then incubated at constant 25° C. until the fragrance ingredient reached equilibrium between the gas and the liquid phase. A defined volume of this saturated headspace (usually 0.5-1 l) was trapped on a micro filter using poly (ethyl-vinyl-benzene-co-divinyl-benzene) porous material, for example Porapak® Q from Supelco, as sorbent. After filter extraction with an appropriate solvent (usually 30-100 µl methyl tert. butyl ether), an aliquot of the extract was analyzed by gas chromatography (GC). Quantification was performed by the external standard calibration method. The concentration in the original headspace can be calculated (in terms of µg/l headspace) from the headspace volume sucked through the micro filter and the aliquot of the filter extract injected into the gas chromatograph. The final equilibrium headspace concentration value of a given test fragrance ingredient is obtained as the mean value of three independent measurements each.

Further information on the technique hereinabove described may be found in: Etzweiler, F.; Senn E. and Neuner-Jehle N., *Ber. Bunsen-Ges. Phys. Chem*. 1984, 88, 578-583.

The olfactive contribution of a fragrance ingredient describes the ingredient's influence on the overall impression of the fragrance composition. The larger the contribution, the more prominent will the olfactive contribution of the fragrance ingredient be in the fragrance composition.

In the context of the present invention, the olfactive contribution of a fragrance ingredient is preferably determined according to the following formula:

olfactive contribution=log (odor value*concentration)

i.e. by multiplying the odor value of the fragrance ingredient by the concentration (typically indicated in wt/wt) of the fragrance ingredient in the fragrance composition and then taking the logarithm of the product. It has been found that the thus obtained value correlates very well with the fragrance ingredient's actual olfactive contribution to the overall impression of the fragrance composition. The use of the logarithm is appropriate to match the response of olfactive receptors in the nose.

Alternatively, the olfactive contribution of a fragrance ingredient could also be determined according to one of the following formulae:

ln (odor value*concentration)
odor value*concentration
odor value*quantityconcentration*log (odor value)
odor value*deposition coefficient
concentration*deposition coefficient odor value*concentration*deposition coefficient
odor value*bloom impact The deposition coefficient is the percentage of a fragrance ingredient that deposits on a substrate in an application, based on the total amount of this fragrance ingredient present in the application. For instance, the application may be washing a substrate with a wash liquor containing the fragrance ingredient, or any other action where a substrate is exposed to a fragrance ingredient-containing product, such as conditioner, shampoo, shower gel, and the like.

The bloom impact is the perceived intensity of a fragrance composition at some distance from the source (for example 1 m) and within a short period of time, for example up to 1 minute, after the conditions at the source have changed. Changing the conditions at the source may include, for example, opening a container comprising a fragrance composition, applying a fragrance composition on a substrate, or diluting a consumer product containing a fragrance composition in water, more particularly in warm water. Blooming is a kinetic effect: it comes early in an application and has a finite, usually short life time, and a sensory effect related to a rapid change of the odorant concentration in the nose.

In the context of the present invention, the total olfactive contribution of a group of fragrance ingredients is the sum of the olfactive contributions of all fragrance ingredients forming said group.

The method of the present invention allows for visualizing the fragrance profile of a fragrance composition taking into account the temporal aspect. The term "temporal fragrance profile", as used throughout this application, refers to the overall olfactive impression of a fragrance composition at various points in time. Typically, the olfactive impression of a fragrance composition will evolve over time, and may even change dramatically, depending on the fragrance ingredients present.

By forming the groups and displaying the total olfactive contributions of the groups in the order of their respective vapor pressures or equilibrium headspace concentrations, it is possible to visualize the evolution of the fragrance profile over time: for example, a high vapor pressure fragrance ingredient may correlate to an early impact and a low vapor pressure to a late impact. In general, the higher the vapor pressure of a fragrance ingredient, the sooner this fragrance ingredient will disappear from the olfactive impression.

As a consequence of the disappearance of the high vapor pressure fragrance ingredients, the equilibrium headspace concentrations of the lower vapor pressure fragrance ingredients increase as time increases. After a certain time, fragrance ingredients having an intermediate vapor pressure also disappear, and the contribution of the fragrance ingredients having the lowest vapor pressures dominates. Thus, the groups may be referred to as temporal groups, because each group impacts the headspace at a different time.

Furthermore, by grouping the fragrance ingredients based on their vapor pressure or equilibrium headspace concentration, it is possible to not only simplify the prediction of the evaporation rate and order, but to also take into account the fact that a fragrance ingredient will typically be noticeable over an extended period of time, overlapping with many other fragrance ingredients, thereby creating a profound olfactive impression.

Thus, the method of the present invention allows for creating a virtual fragrance composition in a visibly impactful form via a GUI (which is software allowing information to be displayed in a graphical/visual form and the user to input a response to that information), thereby enabling a simple, fast, rational and intuitive creation of a fragrance composition. In particular, the very time consuming temporal assessment can be abbreviated and the number of iterations required to achieve a desired result is significantly reduced. Thus, the method of the present invention provides a valuable tool for optimizing or modulating the fragrance profile of a fragrance composition, for instance by harmonizing, boosting, enhancing, balancing, and comparing.

The method of the present invention also facilitates the development of the relationship between the perfumer and a customer by providing a simple and easily understandable means of describing the temporal evolution of a fragrance profile, thereby avoiding barriers to understanding created by technical and somewhat subjective terms typically used by perfumers.

The method of the present invention is advantageously carried out using a local or distributed computing system. This allows for storing information on the fragrance ingredients in a database for retrieval by the processor and for displaying the olfactive contributions on a screen using the GUI.

Such a database may be stored locally or remotely, internally or externally. Preferably, the database contains at least the equilibrium headspace concentration (or other diffusion measure) and odor value of each fragrance ingredient. Advantageously, further information on the fragrance ingredients is stored in the database, such as physical, chemical, biological or sensory attributes that may have a bearing on the olfactive character and/or the olfactive contribution to the overall impression of a fragrance composition; but it may also be general information on the ingredient, such as commercial or regulatory information affecting how and in what quantities it should be used in application.

Such physical or chemical attributes might include properties such as odor detection threshold, polarity, cLogP, solubility, and the like.

Sensory attributes might include the qualitative odor description of an ingredient.

Functional attributes might include the efficacy of an ingredient to alter a mood or behavioural response in a subject after smelling it; or the ability or efficacy of an ingredient to counteract or mask the effects of a source of malodour.

Spatio-temporal performance criteria, such as tenacity, substantivity, bloom, radiance, volume, and trail, may also be incorporated as useful attributes. Optionally, these attributes may be calculated by using suitable algorithms. Examples of suitable algorithms include Vapor Liquid Equilibrium (VLE) calculation and the calculation of the hydrodynamic transport equations for both diffusion and convection regimes.

Tenacity is the property of an ingredient to remain for a certain time on a substrate. The higher the tenacity is, the longer the remanence of the ingredient on that substrate. The tenacity not only depends on the vapor pressure, but also on the existence of specific interactions between the ingredient and the substrate.

Substantivity is governed by tenacity and perception. Tenacious ingredients having low olfactive thresholds are substantive. The substantivity is a key performance indicator for both consumer products and fine fragrance ingredients.

Bloom is the property of an ingredient to generate a strong sensory impact around a perfumed source for a short period of time. Bloom is a key performance indicator for rinse-off products, such as shampoo and shower gel ingredients.

Volume or radiance is the property of an ingredient to be perceived in the air around a perfumed source for a prolonged time. Volume is often referred to as "room filling" and is a key performance indicator for air freshener and fine fragrance ingredients. Trail (or sillage) is the property of an ingredient to be perceived following a moving source perfumed with this ingredient. Trail is influenced by volume and air convection flows.

The ingredients database may further contain general information, such as the chemical composition (i.e. single chemical substance or combination of chemical substances); the chemical formula and structural formula of each chemical substance contained; the origin (natural, semi-synthetic or synthetic); for naturals: the source; the density; the melting point; the boiling point; the partition coefficients, such as air/water partition coefficient, water/oil or water/fat partition coefficients and air/oil or air/fat partition coefficients, and the like; a list of authorized countries; a concentration limit defining a maximum concentration, where applicable for certain countries; the price; the stability; a list of ingredients which are often used in combination with said ingredient; a list of ingredients which are often used as a replacement for said ingredient; typical applications (e.g. personal care fragrance or dairy food); restrictions with regard to formulation (e.g. concerning encapsulation); etc.

The skilled person will appreciate that a database could be populated with all manner of attributes of ingredients that can be measured by analytical or sensory-evaluation techniques generally known in the art.

The database enables the designer to examine the entire palette of fragrance ingredients and compare and contrast their physical, chemical, sensory and functional attributes, such as odor direction, odor family, commercial success, cost attributes, the property of exerting a particularly desirable technical effect, such as malodour-control, or mood-or behavior-modifying effects. In this way, using known clustering programs, the processor can make attribute-based recommendations to a user from the database for the purpose of fragrance formulation design. For example, the processor can access the database to recommend ingredients or a range of ingredients that share one or more attributes or characteristics; or it can recommend ingredients that are responsible for a certain characteristic in a mixture of ingredients; or it can prescribe limits on the amount of an ingredient relevant for a desired characteristic. Furthermore, using pattern recognition, statistical and machine learning techniques, it can compare the palette of ingredients with commercially successful formulae or formulae having other desirable attributes, in order to discover ingredients or clusters of ingredients that are correlated to win-rates. Still further, the attributes for individual ingredients could be normalized against commercial reference ingredients that are interesting for their character, cost or performance, or which are particularly valued by a certain customer.

The database can contain data from a variety of inputs. Its content may also be edited by a user, e.g. by adding additional information, potentially via the GUI. Also, the ingredient record may be automatically complemented by the processor in the computing system, based on the compositions created and/or stored. This may involve a statistical analysis of the compositions.

In a particular embodiment, the total contributions of the groups of fragrance ingredients are displayed in an olfactive space in which the ingredients are shown in their groups and defined by an array of coordinates, each coordinate indicating a specific property of the fragrance ingredients. Preferably, a first coordinate indicates the diffusion measure and a second coordinate indicates the olfactive contribution. For example, the visualization may take the form of a bar chart, with one bar per group of a length that represents the total olfactive contribution. Alternatively or in addition, the temporal fragrance profile may also be displayed as a curve.

Advantageously, each bar is divided into sections (for example each taking up a different portion of the length of the bar) representing the individual fragrance ingredients within that group, for instance by using a different color for each individual fragrance ingredients. Alternatively or in addition, it is also possible to display the different odor families present in the fragrance composition.

In some embodiments, the GUI may also display the fragrance composition in alternative form, to assist the user by presenting further information. For example, the fragrance composition may be shown as circles (of the same color as the equivalent section in the bar chart) in a further two-dimensional olfactive space, with the x-axis indicating the odor threshold and the y-axis indicating the diffusion measure of each individual fragrance ingredient. Any other suitable parameters may be used for display along the two axes. This further two-dimensional olfactive space may be displayed at the same time as the olfactive space with the grouped display (for instance in a side-by-side layout to assist comparison), or at a different time. The olfactive contribution of the fragrance ingredients may be indicated by the size of the circles.

These circles of varying size may instead be freely positioned by the user within the further two-dimensional olfactive space (or within a still further olfactive space) to represent a fragrance in terms of olfactive contribution of the ingredients without odor threshold or diffusion measure information.

The GUI may also display one or more fields in which the user may select one or more fragrances compositions, fragrance ingredients, odor families, groups, or other aspect for display, or apply one or more thresholds to the concentration range or diffusion measures range for display. In a particular embodiment, groups of fragrance ingredients having the same or similar odor values are displayed in one of the fields.

The user may also choose to display (and potentially modify) two fragrances at the same time, while concentrating on a certain odor family in those fragrances only. In a particular embodiment, two or more different fragrance compositions are displayed in the olfactive design space, thereby allowing a comparison of the temporal fragrance profiles.

The user may identify at least one (adjustable) group of fragrance ingredients, the total olfactive contribution of which is too low or too high, respectively, relative to the total olfactive contributions of the other groups. Alternatively, the user may identify a fragrance ingredient within a group that is too low or high with respect to the other fragrance ingredients within its group.

In one embodiment of a method of adjusting the temporal fragrance profile, the GUI accepts user input to change the olfactive contribution of a group or fragrance ingredient or to delete or add a fragrance ingredient within a group. For example, the user may change the length of a bar or section of a bar on a touchscreen (interactive screen), for example by touching and moving the end of a bar or section with a finger and moving the finger to extend or shorten the bar to increase or decrease the olfactive contribution. Equally, dragging a cursor positioned at the end of a bar or section, or using a keyboard could have the same effect. The amount may be "dragged" to zero to remove an ingredient, and a new ingredient within a group may be selected by keyboard/mouse, etc. or touchscreen input. The display of the ingredients in the temporal profile format simplifies the perfumer's job in adjusting or balancing the fragrance composition. Moreover, the olfactive contribution of each group (or even each ingredient) is clearly visualized and this also facilitates the work of the perfumer. Where a change in the grouped display is made, it may automatically update any further olfactive space (for example to remove or add an ingredient or change the size of an olfactive contribution of a specific ingredient or a group of ingredients). Where a further olfactive space is provided, changes may be made by the user with the same mechanisms as discussed above to the length of the bars or the size of the circles provided, or deletion or addition of bars or circles may update the grouped olfactive space. These changes may also be reproduced across to the other olfactive spaces.

When creating a fragrance composition, a perfumer typically aims at creating a certain temporal fragrance profile. Depending on the application, he may wish to create a fragrance composition that will be strongly perceivable immediately after the application, that will be particularly stable over a long period, or that will gradually increase over time, for instance.

The advantageous method of the present invention allows for specifically addressing a certain time range and increasing or decreasing the olfactive impact thereof to modulate the fragrance composition's overall impression. Moreover, it allows for predicting and adjusting the temporal fragrance profile without the necessity of going through many iterations of (physical) creation and long-term assessment. This significantly reduces the time and costs of the creation process and improves sustainability. For the first time, the perfumer can adjust ingredients in a composition whilst directly observing the effect on the temporal profile.

For instance, the perfumer may wish to achieve one or more of the following effects:
  amplification of the total olfactive contribution of a group or of one or more odor families or specific olfactive attributes within a group
  boost of freshness
  little or no deposition
  bloom
  explosion and sustained bloom
  radiation
  linearity Depending on the intended use or application of the fragrance composition, a special temporal fragrance profile may be preferred. For instance, the following effects may be desirable for:
  Fine fragrances: freshness, growing, sustaining.
  Colognes: splash of freshness, mild (almost no) long-lasting.
  Shower gels: immediate boost of freshness, pleasant bloom, as much substantivity on skin as possible.
  Dish-washers: boost of freshness, no substantivity.
  Fabric conditioners: intense signal neat, boost of fresh and clean when opening the washing machine or during hand-washing, pleasant substantive smell on fabric (even after several days).
  Air fresheners: diffusive, blooming, room-filling, pleasant smell.

Depending on the desired temporal fragrance profile, the total olfactive contribution of one or of several groups may be adjusted. Moreover, the total olfactive contribution of one or more groups may be increased, whereas that of one or more other groups may be decreased. The same GUI may be used for modification of the fragrance composition in a database (for instance by changing the details in a spreadsheet form) and/or for providing/updating its display as discussed herein.

There are benefits in the perfumer having access to both the spreadsheet and the visual representation of the temporal profile. For example, the perfumer can look at the fragrance ingredients in the spreadsheet which progressively dominate in the temporal profile. If their concentrations/odor values differ significantly, the perfumer can look to replace one of the fragrance ingredients with a fragrance ingredient having a closer concentration/odor value to the other fragrance ingredients. This process should help to balance the fragrance composition. To this end, it is advantageous to (also) group the fragrance ingredients according to their odor value, for instance in an alternative display mode.

If the total olfactive contribution of a group is changed (rather than an individual fragrance ingredient), the processor may re-calculate the olfactive contribution of each fragrance ingredient within the group so that the same proportions of the fragrance ingredients within the group are maintained (whilst the total olfactive contribution is changed).

Of course the changed display reflects an updated fragrance composition. Advantageously, if the fragrance composition has been retrieved from a database, the changed fragrance composition may be stored (automatically or on request of the user) back into the database, for example with an updated name. In other words, a perfumer may create or amend visually, and then the corresponding calculated values represent the created or amended formula. In a simpler embodiment, a fragrance composition stored in a database (for example in spreadsheet form) may be amended by the user (for example with simple keyboard/mouse input) and then re-loaded into the processor and GUI for display of the temporal profile of the changed fragrance composition.

It is also possible to include a third (z) axis that represents another characteristic parameter, such as an ingredient's clogP. A fourth dimension might be represented by means of color, indicating a particular odor family. The coordinate axes may be linear, logarithmic or whatever else is typically used in the art for a given property or parameter.

In the method of the present invention, groups of fragrance ingredients having the same or a similar diffusion measure are formed. The smaller the range of the diffusion measure in one group, the smaller the number of fragrance ingredients in one group will be and the larger the number of groups. A group may even consist of a single fragrance ingredient.

In a particular embodiment, fragrance ingredients having similar vapor pressures or partial vapor pressures or equilibrium headspace concentrations lying within a certain range are grouped together. Such a range of equilibrium headspace concentrations (or vapor pressures) may span 1 or 2 orders of magnitude, for instance.

Preferably, the equilibrium headspace concentrations or vapor pressures of the fragrance ingredients of each group are within one order of magnitude or less. This allows for a meaningful display of the temporal fragrance profile without excessive details, such that the evolution can easily be grasped at first sight. Each group may follow consecutively from the previous group, so that a range of equilibrium headspace concentrations (for example from >100000 to <1) is covered without gaps. There may be between 5 and 10 groups, preferably 9 in a range between >100000 to <1, in particular when each group covers a different order of magnitude from X to 10X, 10X to 100X etc. The skilled reader will appreciate that the cut-offs between groups are positioned at an appropriate value to give an at least approximately even range of the groups, with overlaps avoided.

Two advantageous ways of grouping the fragrance ingredients based on their equilibrium headspace concentrations are shown in the following table:

|  | Equilibrium Headspace Concentration Range [µg/l] | |
| --- | --- | --- |
| Group I | >100,000 | >10,000 |
| Group II | 10,000-100,000 | 4,000-10,000 |
| Group III | 1,000-10,000 | 1,000-4,000 |
| Group IV | 100-1,000 | 400-1,000 |
| Group V | 10-100 | 100-400 |
| Group VI | 1-10 | 40-100 |
| Group VII | 0.1-1 | 10-40 |
| Group VIII | <0.1 | 1-10 |
| Group IX | — | <1 |

In alternative embodiments, the fragrance ingredients may also be grouped according to their vapor pressure, their retention time on a gas chromatograph, their vapor-liquid-equilibrium (VLE) or based on the maximal abundance time where their abundance in a headspace reaches its maximum.

In a particular embodiment, the method of the present invention further comprises the step of displaying (visualizing) the odor families of the fragrance ingredients. This allows for characterizing the temporal fragrance profile of the fragrance composition in more detail. In particular, it enables the user to analyze and compare the distribution and impact of the different odor families within the different groups, and to identify similarities and/or divergences between the different groups and thus in the fragrance profile over time.

Preferably, the odor families are visualized by means of color coding. This provides an immediate and intuitive impression of the distribution and impact of the odor families, without interfering with the other information displayed. Typical odor families include fruity, green, marine, floral, oriental, woody, mossy, musk, aromatic and citrus.

Alternatively, in the case of an olfactive space defined by an array of coordinates, it is also possible to use one of the coordinates for indicating the odor family.

In a particular embodiment, the individual fragrance ingredients within each group are visualized. This provides an even more detailed visualization of the fragrance compositions' temporal fragrance profile. In particular, the more prominent ingredients (with a greater olfactive contribution) are immediately visible, whereas the more subtle ingredients are also displayed in a more subtle way. This clearly enhances the user experience. It also facilitates the interaction of a perfumer with a customer by providing a detailed visual impression of the fragrance composition.

The present invention provides a method allowing a user to balance the temporal fragrance profile of a fragrance composition comprising a plurality of fragrance ingredients. Said method comprises the steps of:
predicting the temporal fragrance profile of the fragrance composition according to the method of the present invention described above, including the step of visualizing the odor families of the fragrance ingredients;
comparing the odor family distribution within each group of fragrance ingredients to the odor family distribution in the other groups;
identifying at least one balanceable group of fragrance ingredients having a divergent odor family distribution; and
balancing the odor family distribution of the at least one balanceable group.

When creating a fragrance composition, a perfumer typically aims at creating a certain balance of the odor families present, also over time. In most cases, the aim is to maintain more or less the same overall impression over an extended period. But there may also be cases where the perfumer designs a fragrance composition purposefully such that it will change its character significantly over time.

The advantageous method of the present invention allows for visualizing the distribution and impact of the different odor families at a certain point in time, and—by comparison—for identifying and balancing unbalanced groups. Again, the method allows for predicting and adjusting the temporal fragrance profile without the necessity of going through many iterations of (physical) creation and long-term assessment. This significantly reduces the time and costs of the creation process and improves sustainability.

In an embodiment, the method of the present invention is used for visualizing and adjusting the olfactive attributes of the fragrance composition. This allows for an even more targeted modulation of the temporal fragrance profile. The term "olfactive attributes", as used herein, refers to specific olfactive directions within an odor family, such as for example rosy, jasmine or tuberose within floral or apple or raspberry within fruity. In a particular embodiment, the odor family distribution of the at least one balanceable group is balanced by increasing or decreasing the olfactive contribution of at least one fragrance ingredient present in the at least one balanceable group.

Alternatively or in addition, the odor family distribution of the at least one balanceable group is balanced by adding at least one additional fragrance ingredient having an equilibrium headspace concentration corresponding to said at least one balanceable group and/or by removing at least one fragrance ingredient present in the at least one balanceable group.

The perfumer may choose to adjust the olfactive contribution of only a few or even only one fragrance ingredient. But it is also possible that the olfactive contributions of all the fragrance ingredients within one group and odor family or even of several odor families are increased or decreased.

An experienced perfumer will typically know which of the fragrance ingredients within a group and odor family will provide the desired olfactive effect. Alternatively, if the method of the present invention is conducted on a computing system with a database containing information on the fragrance ingredients, the user may obtain certain information from the database.

There now follows a number of particular embodiments and features which apply to each of the methods of the present invention described above.

The methods of the present invention provide a visually impactful depiction of the temporal fragrance profile of a fragrance composition, such that the representation can be thought of as a virtual olfactive fingerprint, or a digital display, of the fragrance composition. This allows the user to avoid compositions that are unbalanced or do not achieve the desired effect, thereby minimizing the number of iterations necessary for creating the final composition, saving time as well as resources.

During the creation process, the perfumer can select ingredients from the database and add them to the olfactive design space. The selection may be carried out using any of the known input means, such as physical manipulation of a touchscreen, via a keyboard, mouse (including other pointers, such as touch pad or stylus), joystick or other such physical input device, or by voice activation means. Input may also be made remotely via an intranet or internet connection, e.g. from a remote computer or smart phone. It is also possible to combine several of these input methods, thereby allowing several users to access the system simultaneously and/or consecutively. This facilitates the collaborative creation of a fragrance composition.

In a particular embodiment, the method of the present invention further comprises the steps of:
  converting, for each fragrance ingredient, its contribution to a corresponding quantity; and
  dispensing and mixing the fragrance ingredients to provide the fragrance composition.

The virtual fragrance composition visualized according to the method of the present invention is sufficient to provide a sample of the fragrance, since it already contains the necessary data, but it can be (back-)converted to spreadsheet form if necessary. The data representing the odor can be used to instruct an odor output device in order to generate the composition. For this purpose, the olfactive contribution of each fragrance ingredient is converted to a corresponding quantity. This conversion can be executed by the same processor as used for the other elements of the method.

The thus determined quantities may be used as a recipe for dispensing and mixing the fragrance ingredients by hand, or they may be transmitted to an output device.

In a particular embodiment, an output device is instructed to dispense and mix the selected fragrance ingredients in the respective quantities, thereby generating the fragrance composition.

To this end, any suitable output device known in the art may be used, for instance a sampling automat such as those typically used in the pharmaceutical industry or a Virtual Aroma Synthesizer (VAS™). U.S. Pat. No. 6,067,842 and US 2005/0244307 describe such Virtual Aroma Synthesizers. Depending on the output device and the fragrance composition, the selected fragrance ingredients may be filled into a receptacle, or vaporized, or ablated from an ingredient reservoir using a stream of air, or sprayed from a pump, or atomized.

The sampling automat is typically provided with a plurality of fragrance ingredients (preferably all) and is able to prepare a sample of the fragrance composition by taking up the quantity of each fragrance ingredient indicated in the production file and mix it with the other fragrance ingredients.

The fragrance composition is advantageously created using an output device proximate to the computing device, thereby providing immediate feedback to the user. This allows the user to explore a vast array of ideas instantaneously. Furthermore, it improves the interaction of the user with a customer, as it enables the user to adjust the selected fragrance ingredients and/or their olfactive contributions according to the customer's desires and to almost instantaneously create modification to a fragrance composition.

Alternatively or in addition, the calculated quantities of the selected ingredients may be sent via electronic means to another location, where the fragrance composition is created. This allows for an easy sharing of the composition with co-workers, evaluators, and/or customers. In another aspect, the present invention provides a fragrance composition comprising a plurality of fragrance ingredients, wherein the fragrance composition is obtained by the method of the present invention.

The fragrance compositions created or visualized according to the methods of the present invention are advantageously stored in the database. It is also possible to store fragrance compositions otherwise generated in the database. By storing complete compositions in the database, it is possible to use them as a starting point for a subsequent new composition or compare several compositions.

According to a further aspect of the invention, there is provided a computer apparatus arranged to carry out a method of predicting the temporal fragrance profile of a fragrance composition comprising a plurality of fragrance ingredients, the computer apparatus comprising a processor to: retrieve a diffusion measure of how fast each fragrance ingredient diffuses into a headspace; form groups of fragrance ingredients having the same or a similar diffusion measure; determine the olfactive contribution of each fragrance ingredient; calculate the total olfactive contribution of a group of fragrance ingredients as the sum of the olfactive contributions of all fragrance ingredients forming said group; and comprising a graphical user interface to display the total olfactive contribution of each group of fragrance ingredients in the order of their respective diffusion measures to visualize the temporal fragrance profile of the fragrance composition.

All of the sub-aspects of the method are equally applicable to the apparatus aspect. A computer program according to preferred embodiments of the present invention may comprise any combination of the apparatus and method aspects. Methods or computer programs according to further embodiments may be described as computer-implemented in that they require processing and memory capability.

The computer apparatus (terminal or system) according to preferred embodiments is described as configured or arranged to, or simply "to" carry out certain functions. This configuration or arrangement could be by use of hardware or middleware or any other suitable system. In preferred embodiments, the configuration or arrangement is by software. According to a further aspect there is provided a program which, when loaded onto at least one computer apparatus, configures the at least one computer apparatus to carry out the method steps according to any of the preceding method definitions or any combination thereof.

In general the computer apparatus may comprise the elements listed as being configured or arranged to provide the functions defined. For example, this computer apparatus may include memory, processing, a user interface and a network interface.

The invention may be implemented in digital electronic circuitry, or in computer hardware, firmware, software, or in combinations of them. The invention may be implemented as a computer program or computer program product, i.e., a computer program tangibly embodied in a non-transitory information carrier, e.g., in a machine-readable storage device, or in a propagated signal, for execution by, or to control the operation of, one or more hardware modules.

A computer program may be in the form of a stand-alone program, a computer program portion or more than one computer program and may be written in any form of programming language, including compiled or interpreted languages, and it may be deployed in any form, including as a stand-alone program or as a module, component, subroutine, or other unit suitable for use in a data processing environment. A computer program may be deployed to be executed on one module or on multiple modules at one site or distributed across multiple sites and interconnected by a communication network. Method steps of the invention may be performed by one or more programmable processors executing a computer program to perform functions of the invention by operating on input data and generating output. The apparatus of the invention may be implemented as programmed hardware or as special purpose logic circuitry, including e.g., an FPGA (field programmable gate array) or an ASIC (application-specific integrated circuit).

Processors suitable for the execution of a computer program include, by way of example, both general and special purpose microprocessors, and any one or more processors of any kind of digital computer apparatus. Generally, a processor will receive instructions and data from a read-only memory or a random access memory or both. The essential elements of a computer apparatus are a processor for executing instructions coupled to one or more memory devices for storing instructions and data.

The invention is described in terms of particular embodiments. Other embodiments are within the scope of the following claims. For example, the steps of the invention may be performed in a different order and still achieve desirable results. Multiple test script versions may be edited and invoked as a unit without using object-oriented programming technology; for example, the elements of a script object may be organized in a structured database or a file system, and the operations described as being performed by the script object may be performed by a test control program.

Elements of the invention have been described using the terms "processor", "GUI", "user input means", etc. The skilled person will appreciate that such functional terms and their equivalents may refer to parts of the system that are spatially separate but combine to serve the function defined. Equally, the same physical parts of the system may provide two or more of the functions defined. More than one functionality may be provided by a functional component. For instance, the user input means may allow user input via a touchscreen, using an internet link to another user location, and using a keyboard and/or mouse.

For example, separately defined means may be implemented using the same memory and/or processor as appropriate and different processors may be used together as the "processor" defined in the claims.

The present invention will be further illustrated by means of the following examples and attached figures, in which.

Figure 4:
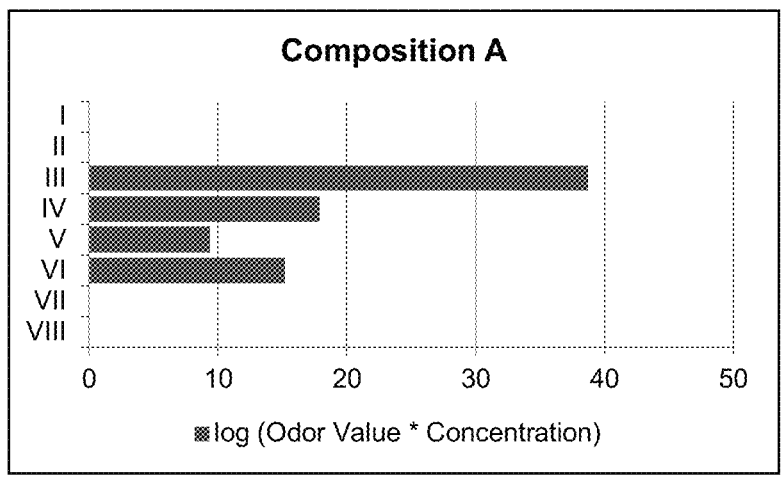
Figure 5:
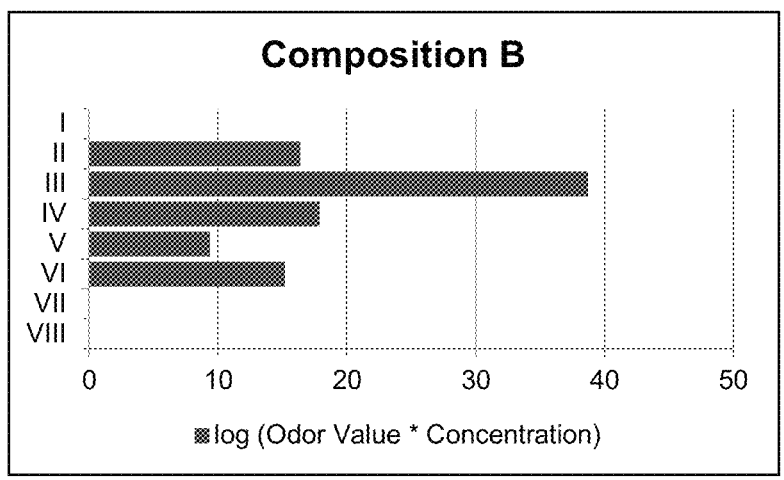
Figure 6:
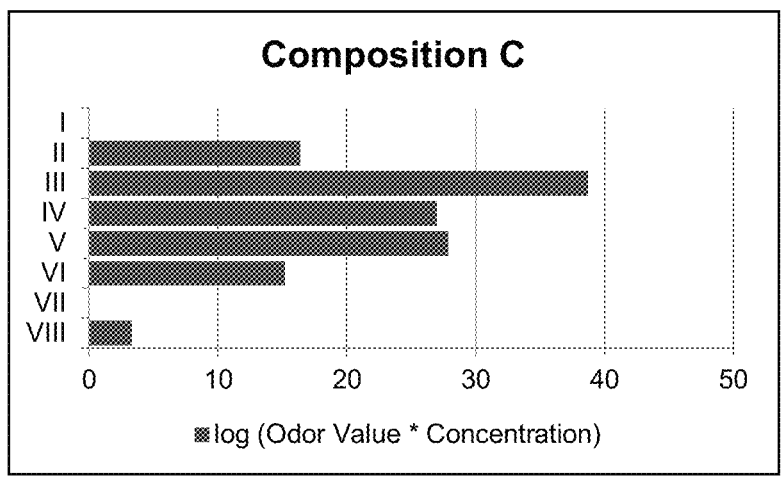
Figure 7:
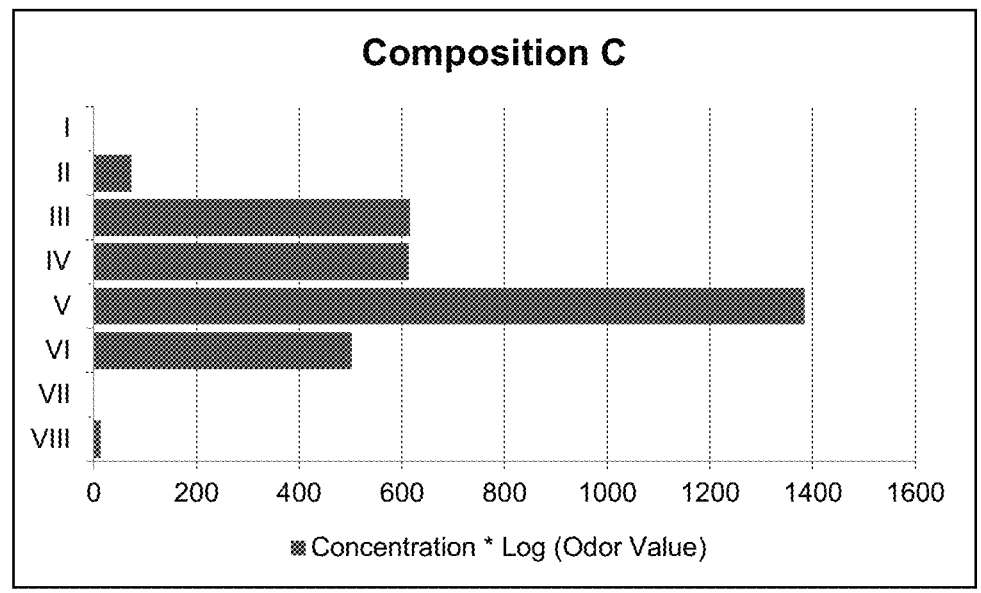
Figure 8:
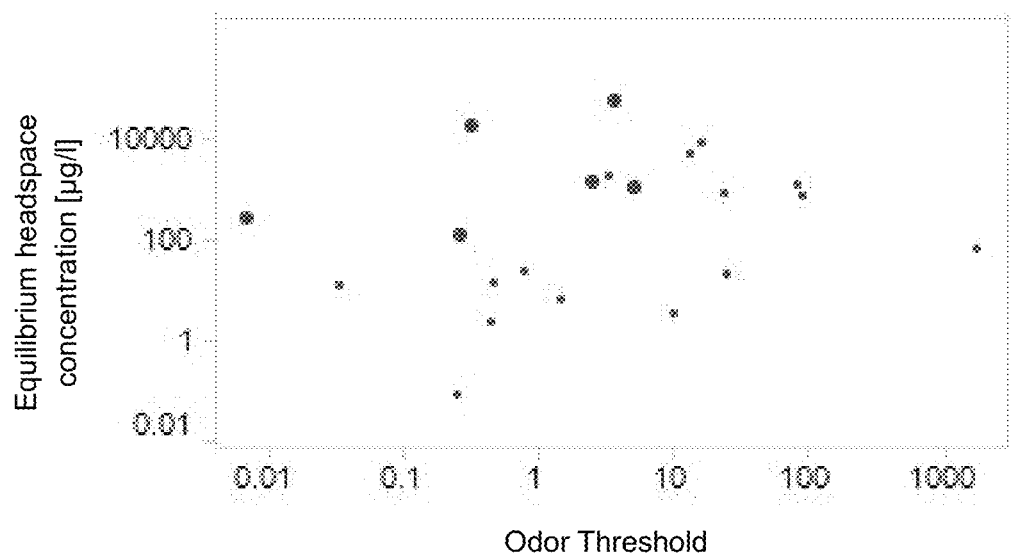
Figure 9:
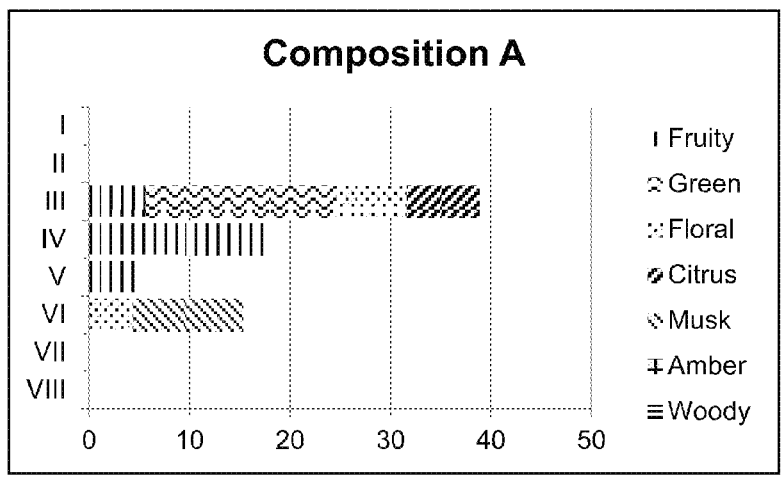
Figure 10:
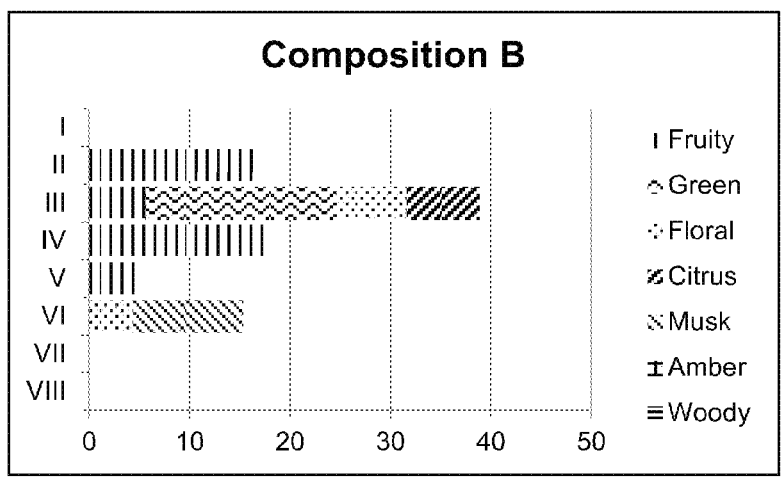
Figure 11:
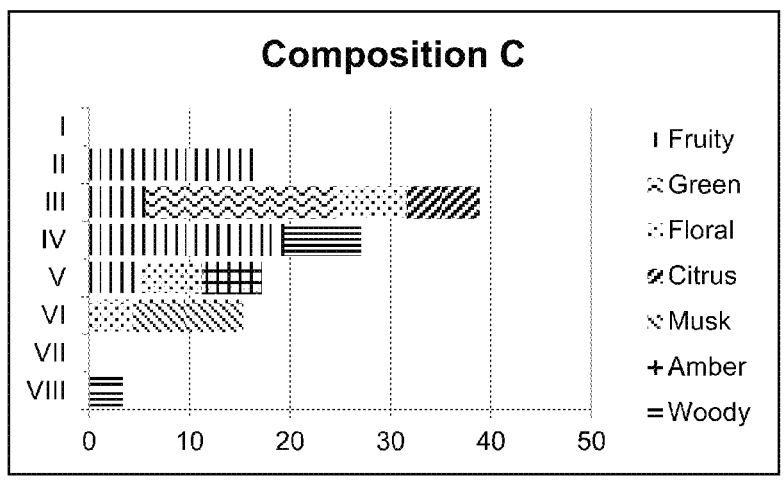
Figure 12:
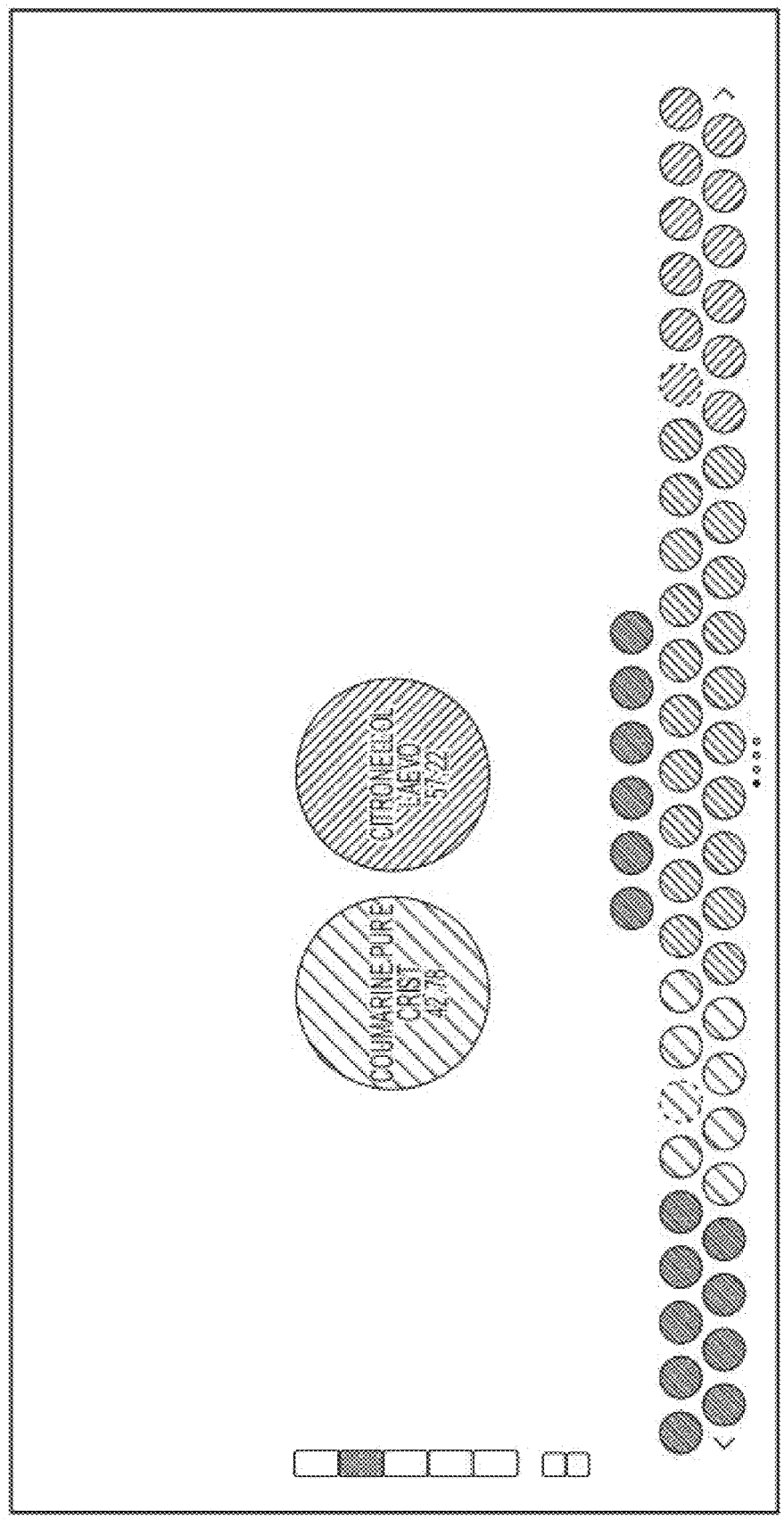
Figure 13:
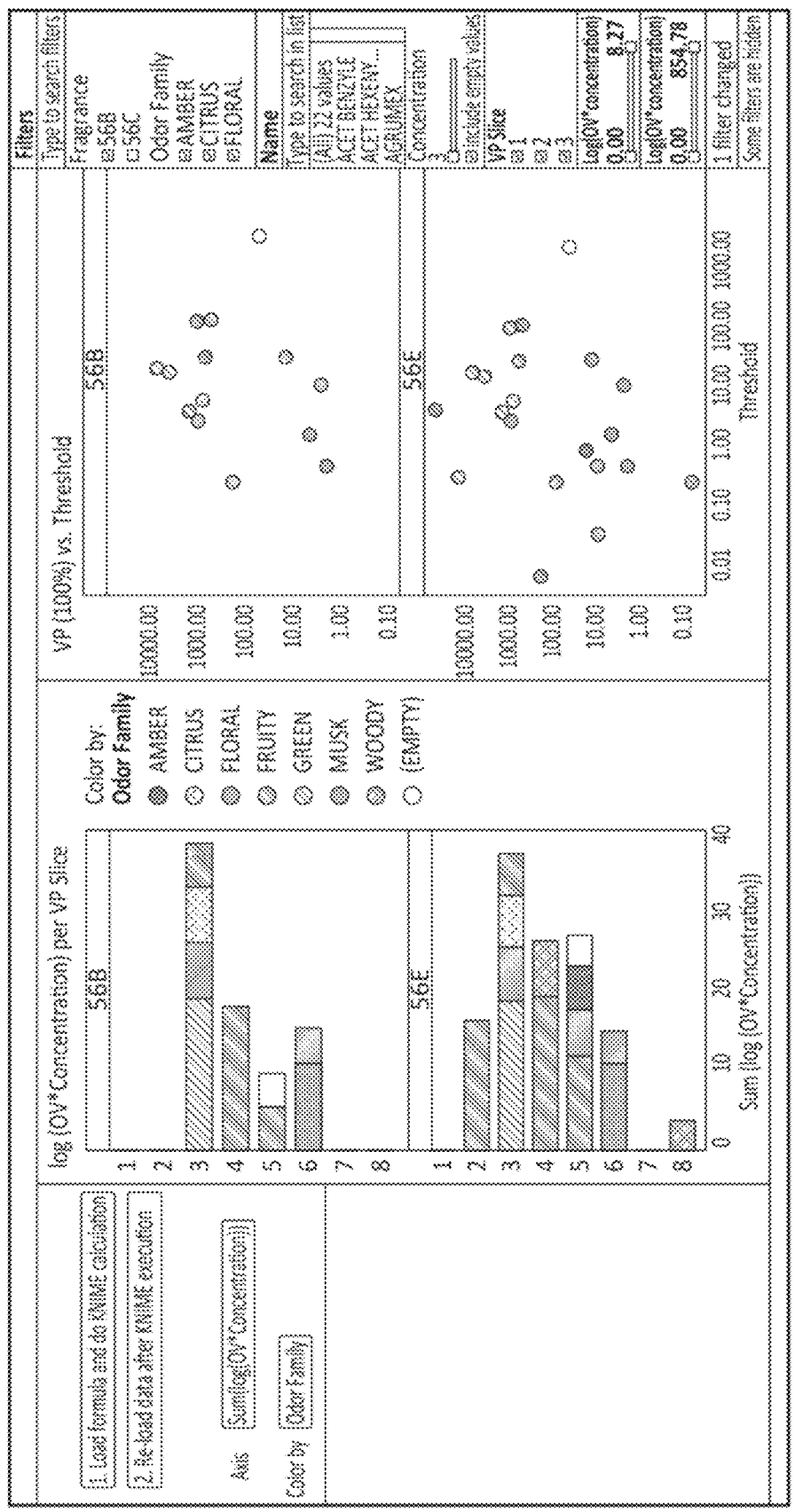
Figure 15:
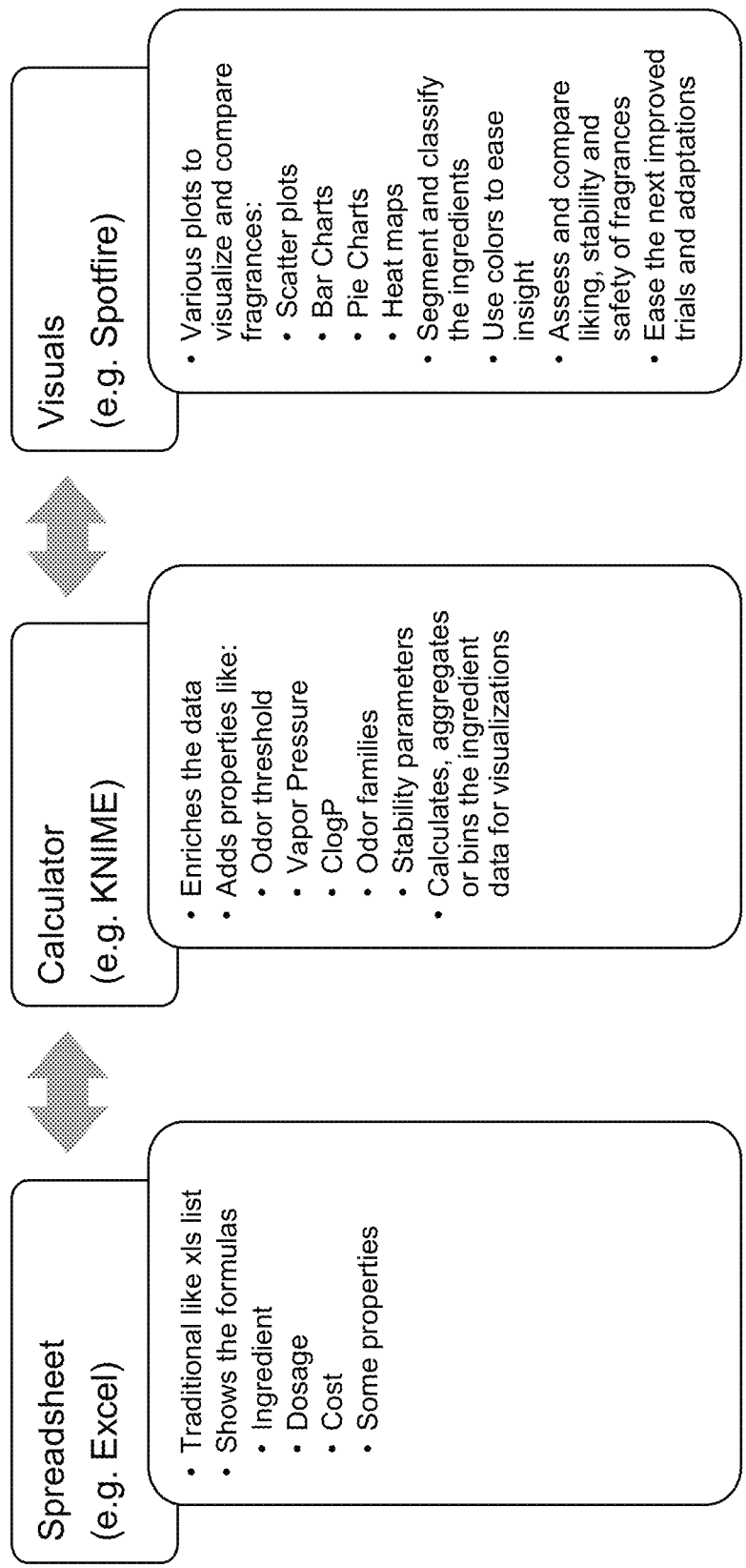
Figure 16:
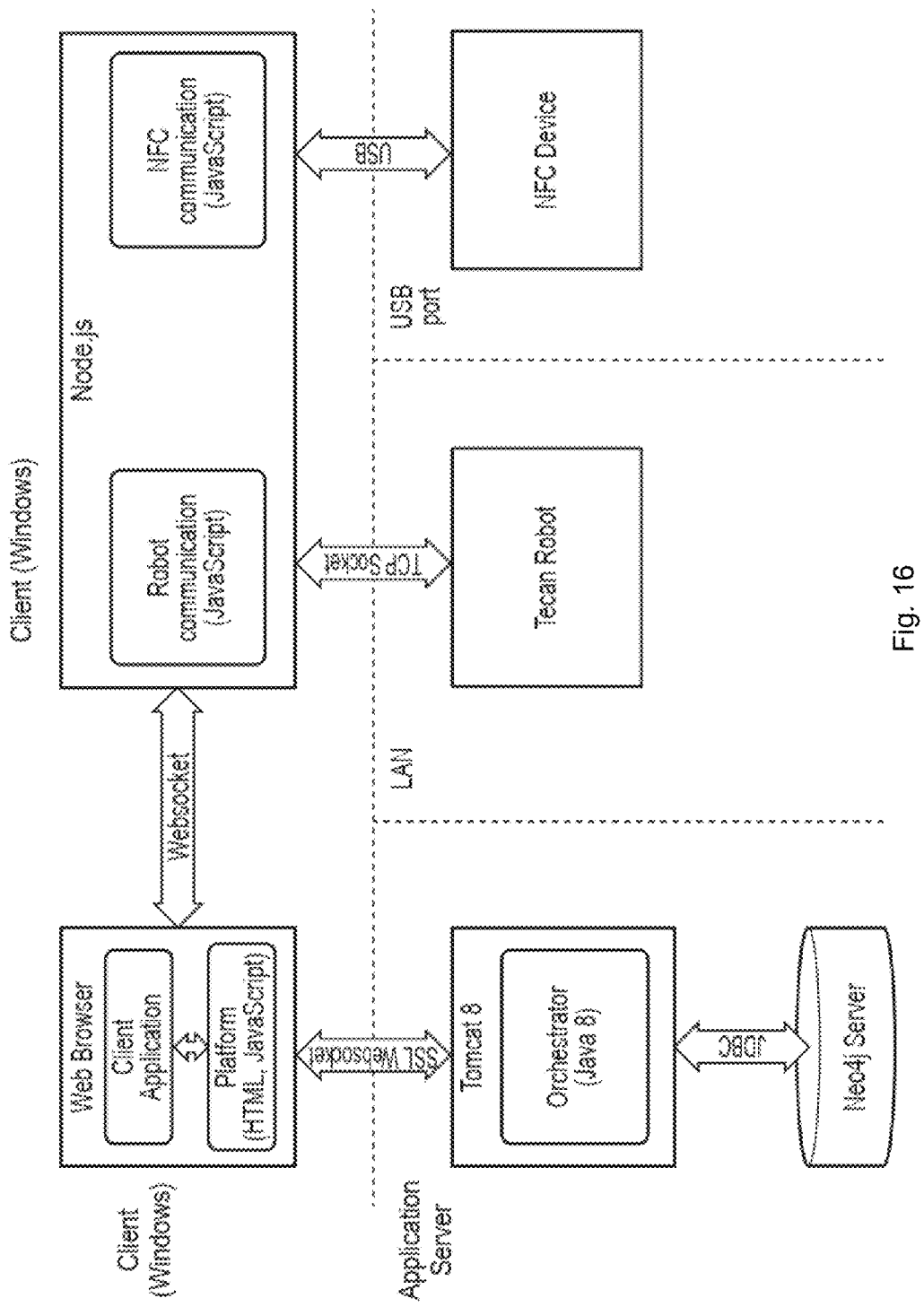

FIG. 4 provides a visualization of the temporal fragrance profile of composition A;

FIG. 5 provides a visualization of the temporal fragrance profile of composition B;

FIG. 6 provides a visualization of the temporal fragrance profile of composition C;

FIG. 7 provides an alternative visualization of the temporal fragrance profile of composition C;

FIG. 8 is an excerpt from a display showing fragrance ingredients of Composition C as circles;

FIG. 9 provides a visualization of the temporal fragrance profile of composition A including indication of the odor families;

FIG. 10 provides a visualization of the temporal fragrance profile of composition B including indication of the odor families;

FIG. 11 provides a visualization of the temporal fragrance profile of composition C including indication of the odor families;

FIG. 12 shows a further visualization of a simple composition in a further olfactive space;

FIG. 13 is a view of a GUI including a temporal visualization and a threshold visualization for two fragrance compositions;

FIGS. 14a and 14b show a spreadsheet showing a fragrance composition;

FIG. 15 is a schematic view of a simple implementation of an embodiment including use of commercially available software;

FIG. 16 is a conceptual diagram of a suitable application architecture; and

FIG. 17 is a conceptual diagram of a suitable server architecture.

GENERAL EMBODIMENT

Figure 1:
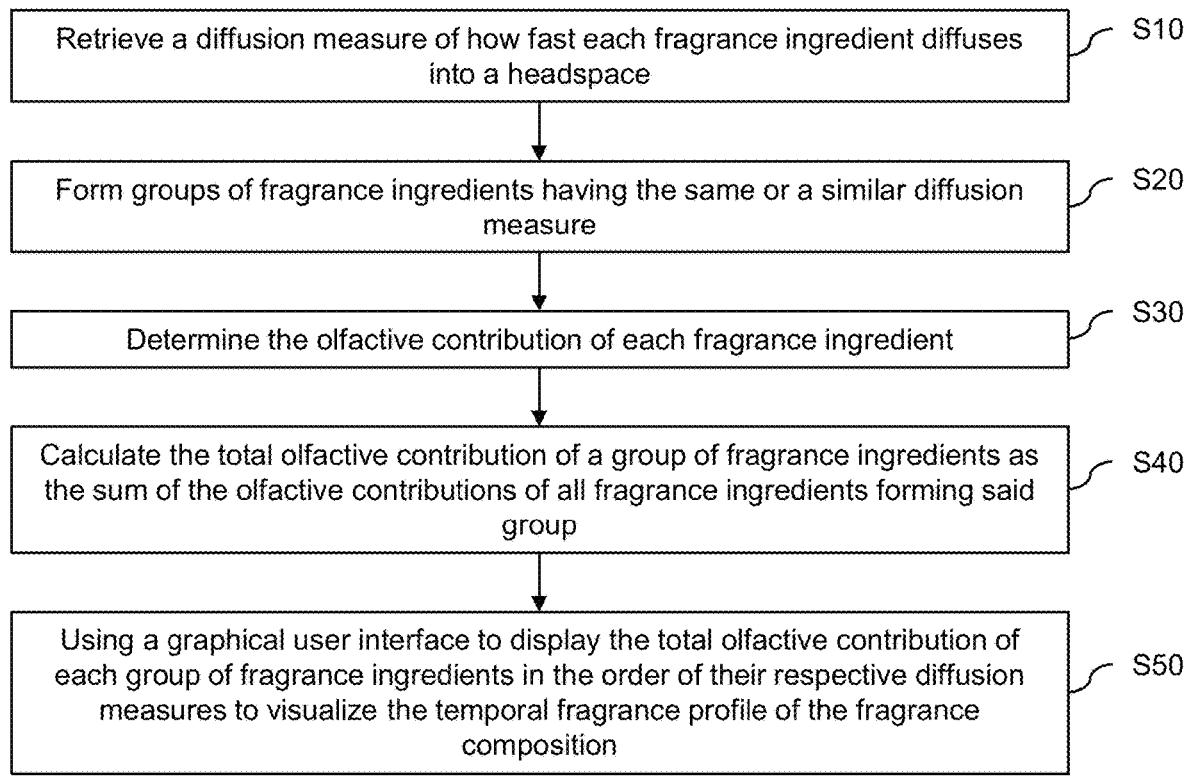
FIG. 1 is a flowchart of an embodiment.

FIG. 1 is a flow chart depicting a computer-implemented method of predicting the temporal fragrance profile of a fragrance composition comprising a plurality of fragrance ingredients. In S10, the processor retrieves a diffusion measure of how fast each fragrance ingredient diffuses into a headspace (from a database or by calculation). In step S20, the processor forms groups of fragrance ingredients having the same or a similar diffusion measure. An indication of the group that a fragrance ingredient belongs to may be stored in the details for that fragrance ingredient in the database. In step S30, the processor retrieves (or calculates) the olfactive contribution of each fragrance ingredient. In step S40, the processor calculates the total olfactive contribution of a group of fragrance ingredients as the sum of the olfactive contributions of all fragrance ingredients forming said group. Once these values have been produced, there is a display step S50, in which a GUI is used to display the total olfactive contribution of each group of fragrance ingredients in the order of their respective diffusion measures to visualize the temporal fragrance profile of the fragrance composition.

Further optional steps may include use of the GUI to change an olfactive contribution of a group or fragrance ingredient, or to delete or add a fragrance ingredient. These further steps may adjust or balance a fragrance composition or create a new fragrance composition.

Figure 2:
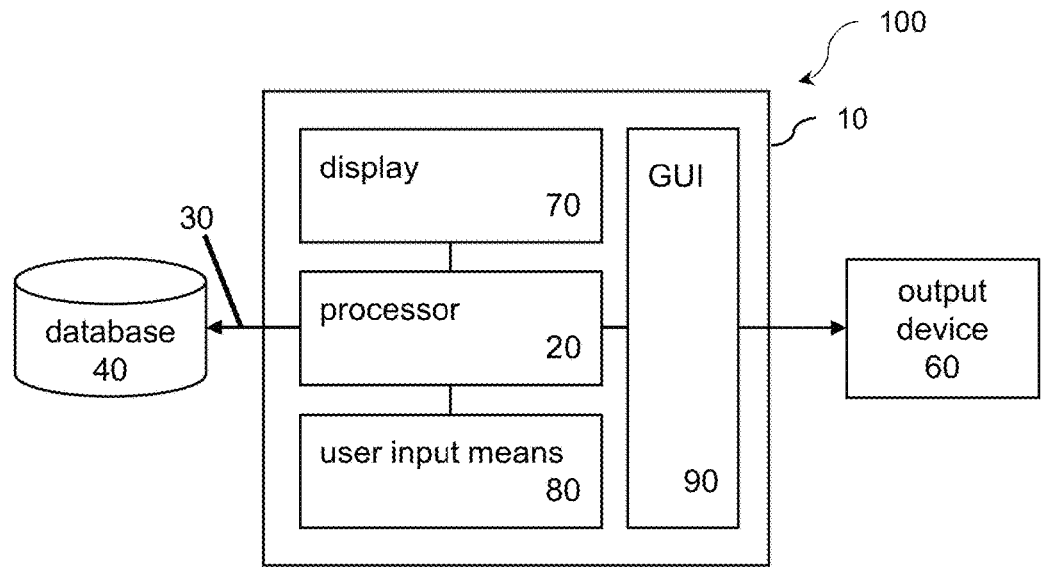
FIG. 2 is a block diagram of a computer apparatus according to an embodiment.

FIG. 2 shows a computer apparatus 10 arranged to allow a user to view, amend and potentially produce (dispense) a fragrance composition. The terminal includes a processor 20, a possible database connection 30 to a database 40 storing fragrance ingredients, and an optional output connection to an output device 60 configured to produce a sample of the fragrance composition, and a display 70 which is controlled by a graphical user interface, GUI 90. There may also be provided an input means linked to the GUI 90, preferably a user input means 80. The processor may be configured to accept selection and adjustment of fragrance ingredients from the database via the user input means. The input means may include a touchscreen also acting as the display and/or a keyboard/mouse and/or other local or remote means, such as a link to a database storing compositions.

The GUI adds bar charts and/or pictograms representing grouped selected fragrance ingredients in an olfactive space on the display. The grouping is by a diffusion measure, as explained previously. The total olfactive contribution for each group may be shown by means of length of the bar for that group in the bar chart, or size of the pictograms (such as circles). The GUI may also show different views of the fragrance composition in further olfactive spaces.

The processor may also convert, for each selected fragrance ingredient, its olfactive contribution to a corresponding quantity of the fragrance ingredient. In this case, the quantity is often expressed as a percentage of the full fragrance composition (and is expressed in absolute terms at the latest at the output stage). As for the other steps carried out by the processor, conversion can be local, or use input from an application running on the cloud. If the user requests a sample of the fragrance composition via the input means, the processor instructs the output device to dispense the corresponding quantity (according to the respective proportions) of the selected fragrance ingredients.

Figure 3:
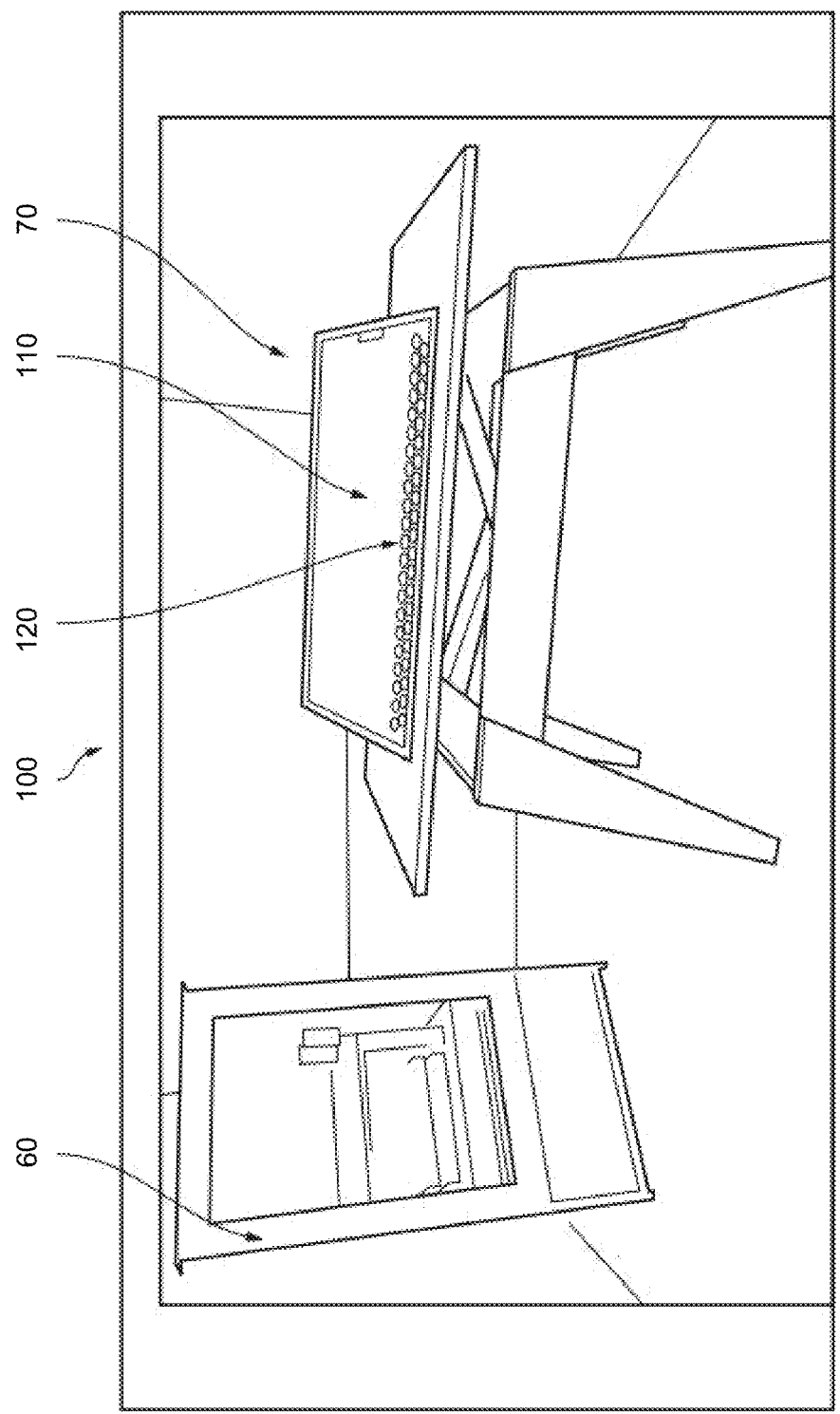
FIG. 3 is a view showing the layout of a system according to an invention embodiment.

FIG. 3 shows the layout of a system 100, including a touchscreen 70 acting as the display and as one user input means 80. The output device 60 is depicted to the left at the same location. A keyboard and mouse and a processor, links to external processing capability and links between the parts are not shown, for simplicity. The touchscreen is displaying a selection menu 120 in a first section, to the bottom of the screen and an olfactive design space 110 in a second section in the main part of the screen. The design space is empty, but the selection menu includes two rows of circular icons/pictograms each representing a fragrance ingredient or pre-defined group of fragrance ingredients that may be selected to create a fragrance composition. The user may switch between screens with the different olfactive spaces mentioned previously.

EXAMPLE 1: GROUPING OF FRAGRANCE INGREDIENTS

In order to predict the temporal fragrance profile of the fragrance compositions A, B, and C described below, the fragrance ingredients were grouped based on their equilibrium headspace concentration into the following eight groups:

|  | Equilibrium Headspace Concentration Range [µg/l] |
|---|---|
| Group I | >100,000 |
| Group II | 10,000-100,000 |
| Group III | 1,000-10,000 |
| Group IV | 100-1,000 |
| Group V | 10-100 |
| Group VI | 1-10 |
| Group VII | 0.1-1 |
| Group VIII | <0.1 |

EXAMPLE 2: VISUALIZATION OF TEMPORAL FRAGRANCE PROFILE

Fragrance composition C (see Table 1 below) was visualized in four different manners shown in FIGS. 6 to 8 and 11:

FIG. 8 displays the individual fragrance ingredients as circles in a two-dimensional olfactive space, with the x-axis indicating the odor threshold and the y-axis indicating the equilibrium headspace concentration of the fragrance ingredients. The olfactive contribution of the fragrance ingredients is indicated by the size of the circles.

FIG. 6 provides a display with a first visualization of the temporal fragrance profile of composition C. The olfactive contributions of the fragrance ingredients were determined as log (odor value*concentration) and then added up for each group to obtain the total olfactive contribution of each group. The total olfactive contributions are displayed as bars in a two-dimensional olfactive space, with the x-axis indicating the total olfactive contribution and the y-axis indicating the group attributed based on the equilibrium headspace concentration range (see Example 1). The lower-numbered groups diffuse into the headspace first. The longer the bar, the higher the total olfactive contribution. The bars may also be displayed to distinguish between the different ingredients falling within the group, or by odor family, using color or shading, for example.

In FIG. 6, Composition C has olfactive contributions in groups II to VI and a low olfactive contribution in group VIII.

Different profiles are required for different products. For example, a dishwasher tablet may require a fragrance including only early-developing groups I to III. A candle fragrance may include groups III to VII. The designer may wish to change the intensity and character of the profile over time, or to keep it as constant as possible.

The user may adjust the length of the bars to change the olfactive contribution.

FIG. 7 provides an alternative visualization of the temporal fragrance profile of composition C, displaying concentration*log (odor value) on the x-axis and the group attributed based on the equilibrium headspace concentration range (see Example 1) on the y-axis.

FIG. 11 provides a more detailed visualization of the temporal fragrance profile of composition C, further indicating the odor families of the fragrance ingredients using shading (for better reproduction in black and white).

The visualizations of FIGS. 6, 7, and 11 can be interpreted in a very intuitive fashion and provide an accurate prediction of the temporal fragrance profile of fragrance composition C. Going from group I to VIII, the total olfactive contribution of each of the groups indicates the olfactive impression at a certain point in time after application. Furthermore, FIG. 11 provides an even more detailed characterization of the fragrance profile by indicating the odor families present in each group.

EXAMPLE 3: ADJUSTING THE TEMPORAL FRAGRANCE PROFILE

FIGS. 4, 5, and 6, respectively, visualize the temporal fragrance profiles of three relatively similar fragrance compositions A, B, and C (see Table 2 below).

The total olfactive contributions of each of the groups are displayed as bars in a two-dimensional olfactive space, with the x-axis indicating the total olfactive contribution and the y-axis indicating group attributed based on the equilibrium headspace concentration range, to visualize the temporal fragrance profiles.

TABLE 1

Fragrance Composition C:

| Ingredient | Equilibrium Headspace Concentration [μg/l] | Group | Odor Value | Concentration (wt/wt) [%] | log (Odor Value * Concentration) | Concentration * log (Odor Value) | Odor Family |
|---|---|---|---|---|---|---|---|
| benzyl acetate | 931 | IV | 40913 | 20 | 5.9 | 92 | FRUITY |
| (Z)-hex-3-en-1-yl acetate | 8931 | III | 575466 | 3 | 6.2 | 17 | GREEN |
| 2-(tert-butyl)cyclohexyl acetate (AGRUMEX) | 773 | IV | 8764 | 40 | 5.5 | 158 | FRUITY |
| (E)-2-benzylideneoctanal (ALPHA HEXYL CINNAMIC ALDEHYDE) | 4 | VI | 384 | 50 | 4.3 | 129 | FLORAL |
| 1-(2,6,6-trimethyl-1-cyclohex-3-enyl)but-2-en-1-one (DAMASCONE DELTA) | 267 | IV | 39868000 | 3 | 8.1 | 23 | FRUITY |
| 2,6-dimethyloct-7-en-2-ol (DIHYDRO MYRCENOL) | 1200 | III | 238151 | 50 | 7.1 | 269 | CITRUS |
| dipropylene glycol | 70 | V | 41 | 375 | 4.2 | 605 | — |
| methyl 2,4-dihydroxy-3,6-dimethylbenzoate (EVERNYL) | 0.1 | VIII | 368 | 5 | 3.3 | 13 | WOODY |
| (Z)-hex-3-en-1-ol | 5211 | III | 391561 | 3 | 6.1 | 17 | GREEN |
| (E)-4-(2,6,6-trimethylcyclohex-1-en-1-yl)but-3-en-2-one (IONONE BETA) | 125 | IV | 484850 | 60 | 7.5 | 341 | WOODY |
| 1-(2,3,8,8-tetramethyl-1,2,3,4,5,6,7,8-octahydronaphthalen-2-yl)ethanone (ISO E SUPER) | 25 | V | 32556 | 20 | 5.8 | 90 | AMBER |
| 2-(phenoxy)ethyl 2-methylpropionate | 20 | V | 816 | 140 | 5.1 | 408 | FRUITY |
| 3-(4-(tert-butyl)phenyl)-2-methylpropanal (LILIAL) | 15 | V | 32978 | 50 | 6.2 | 226 | FLORAL |
| 3,7-dimethylocta-1,6-dien-3-ol (LINALOOL) | 1408 | III | 587273 | 30 | 7.2 | 173 | FLORAL |
| ethyl 2-methylpentanoate (MANZANATE) | 18995 | II | 62586532 | 3 | 8.3 | 23 | FRUITY |
| ethyl 2-methylbutanoate | 59643 | II | 16577930 | 7 | 8.1 | 51 | FRUITY |
| prop-2-enyl heptanoate ALLYL OENANTHATE | 1345 | III | 16391 | 25 | 5.6 | 105 | FRUITY |
| 5-heptyldihydrofuran-2(3H)-one PEACH PURE | 13 | V | 407972 | 10 | 6.6 | 56 | FRUITY |
| 2-(1-(3,3-dimethylcyclohexyl)ethoxy)-2-methylpropyl cyclopropanecarboxylate (SERENOLIDE) | 3 | VI | 6014 | 60 | 5.6 | 227 | MUSK |
| oxacyclohexadecan-2-one (THIBETOLIDE) | 7 | VI | 4682 | 40 | 5.3 | 147 | MUSK |
| 2,4-dimethylcyclohex-3-enecarbaldehyde (TRICYCLAL) | 1926 | III | 585468 | 6 | 6.5 | 35 | GREEN |

TABLE 2

Fragrance Compositions A, B, and C:

| Ingredient | Equilibrium Headspace Concentration [ug/l] | Group | Odor Value | Concentration in Composition A [%] | Concentration in Composition B [%] | Concentration in Composition C [%] |
|---|---|---|---|---|---|---|
| benzyl acetate | 931 | IV | 40913 | 20 | 20 | 20 |
| (Z)-hex-3-en-1-yl acetate | 8931 | | 575466 | 3 | 3 | 3 |
| 2-(tert-butyl)cyclohexyl acetate (AGRUMEX) | 773 | IV | 8764 | 40 | 40 | 40 |
| (E)-2-benzylideneoctanal (ALPHA HEXYL CINNAMIC ALDEHYDE) | 4 | VI | 384 | 50 | 50 | 50 |
| E)-1-(2,6,6-trimethylcyclohex-2-en-1-yl)but-2-en-1-one (DAMASCONE ALPHA) | 242 | IV | 959621 | 3 | 3 | — |
| 1-(2,6,6-trimethyl-1-cyclohex-3-enyl)but-2-en-1-one (DAMASCONE DELTA) | 267 | IV | 39868000 | — | — | 3 |
| 2,6-dimethyloct-7-en-2-ol (DIHYDRO MYRCENOL) | 1200 | | 238151 | 50 | 50 | 50 |
| dipropylene glycol | 70 | V | 41 | 530 | 520 | 375 |

TABLE 2-continued

Fragrance Compositions A, B, and C:

| Ingredient | Equilibrium Headspace Concentration [ug/l] | Group | Odor Value | Concentration in Composition A [%] | Concentration in Composition B [%] | Concentration in Composition C [%] |
|---|---|---|---|---|---|---|
| methyl 2,4-dihydroxy-3,6-dimethylbenzoate (EVERNYL) | 0.1 | 8 | 368 | — | — | 5 |
| (Z)-hex-3-en-1-ol | 5211 | III | 391561 | 3 | 3 | 3 |
| (E)-4-(2,6,6-trimethylcyclohex-1-en-1-yl)but-3-en-2-one (IONONE BETA) | 125 | IV | 484850 | — | — | 60 |
| 1-(2,3,8,8-tetramethyl-1,2,3,4,5,6,7,8-octahydronaphthalen-2-yl)ethanone (ISO E SUPER) | 25 | V | 32556 | — | — | 20 |
| 2-(phenoxy)ethyl 2-methylpropionate | 20 | V | 816 | 140 | 140 | 140 |
| 3-(4-(tert-butyl)phenyl)-2-methylpropanal (LILIAL) | 15 | V | 32978 | — | — | 50 |
| 3,7-dimethylocta-1,6-dien-3-ol (LINALOOL) | 1408 | V | 587273 | 30 | 30 | 30 |
| ethyl 2-methylpentanoate (MANZANATE) | 18995 | II | 62586532 | — | 3 | 3 |
| ethyl 2-methylbutanoate | 59643 | II | 16577930 | — | 1 | 7 |
| prop-2-enyl heptanoate ALLYL OENANTHATE | 1345 | | 16391 | 25 | 25 | 25 |
| 5-heptyldihydrofuran-2(3H)-one PEACH PURE | 13 | V | 407972 | — | — | 10 |
| 2-(1-(3,3-dimethylcyclohexyl)ethoxy)-2-methylpropyl cyclopropanecarboxylate (SERENOLIDE) | 3 | VI | 6014 | 60 | 60 | 60 |
| oxacyclohexadecan-2-one (THIBETOLIDE) | 7 | VI | 4682 | 40 | 40 | 40 |
| 2,4-dimethylcyclohex-3-enecarbaldehyde (TRICYCLAL) | 1926 | III | 585468 | 6 | 6 | 6 |

Adjusting the Temporal Fragrance Profile

Together, FIGS. 4, 5, and 6 illustrate the adjustment and balancing of a fragrance composition suitable for use in a shampoo, for instance, going from composition A via B to C.

Fragrance composition A provides a direct fruity apple accord, having a classic fragrance profile often used as a core shampoo smell.

By comparison, fragrance composition B further includes volatile and low odor threshold fragrance ingredients. By the introduction of these fragrance ingredients, the performance of the accord is significantly improved at the neat and initial bloom stages.

In the last step going from fragrance composition B to fragrance composition C, middle and low volatility fragrance ingredients are introduced. This enhances the overall performance and perceived "depth" of the accord in use is significantly, in particular during the showering, lathering, rinsing, and final perception on wet and dry hair or skin.

EXAMPLE 4: BALANCING THE TEMPORAL FRAGRANCE PROFILE

FIGS. 9, 10, and 11, respectively, visualize the temporal fragrance profiles of the same three fragrance compositions A, B, and C (see Table 2 above).

Again, the total olfactive contributions of each of the groups are displayed as bars in a two-dimensional olfactive space, with the x-axis indicating the total olfactive contribution and the y-axis indicating group attributed based on the equilibrium headspace concentration range, to visualize the temporal fragrance profiles.

In addition, the odor families of the fragrance ingredients are indicated for each group.

Balancing the Temporal Fragrance Profiles

FIGS. 9, 10, and 11 provide a more specific visualization of the process described in example 3 above, indicating the different odor families present.

Fragrance composition A illustrates a direct fruity apple accord, giving a classic, and core shampoo smell.

In fragrance composition B, volatile and low odor threshold fragrance ingredients have been introduced, providing a definite juicy, fruity smell of over-ripe apple. In particular, the immediate impression of the accord in direct contact, i.e. in neat and at the initial use phase while diluting in water under the shower, is clearly enhanced in intensity and also in conveying a clean, fresh, fruity, juicy pleasant olfactive signal to the user.

In the last step, by introducing some fruity, floral and woody fragrance ingredients having middle and low volatility, the key fruity apple character is reinforced and maintained during the all in-use experience. In addition, the overall fragrance impression is now more complex, more sophisticated and longer lasting.

Additional Figures

The screen view of FIG. 12 shows a different olfactive (or design) space. Each available fragrance ingredient is represented by a pictogram in a selection menu to the bottom of the screen. The larger the pictogram, the greater the influence of the fragrance ingredient in the fragrance composition. Conversely, the smaller the pictogram, the smaller the influence of the fragrance ingredient in the fragrance composition. The available space may be too small to accommodate all the fragrance ingredients, in which case only some of the fragrance ingredients are visible at a time. A user can request the display of the remaining pictograms, e.g. by sliding left or right to move along the list of fragrance ingredients using the arrows shown.

The pictograms (whether in the olfactive space or in the selection menu) are color coded i.e. the pictograms of fragrance ingredients belonging to the same odor family are illustrated by the same or a similar color. For example, pictograms of fragrance ingredients belonging to the family "Herbal" may have a light green background. In the same manner, pictograms of fragrance ingredients belonging to the family "Woody" may have a brown background. After selection, the color of a fragrance ingredient is darkened in the selection menu.

In FIG. 12, the user has selected two fragrance ingredients by "moving" them from the selection menu to the design space to add them to the fragrance composition being created. The original olfactive contribution value of each fragrance ingredient is set to 1000000 or another default value This means that, without adjustment, the olfactive contribution of each selected fragrance ingredient to the fragrance composition is equal and each fragrance ingredient has the same size pictogram. The number below the fragrance ingredient names shown in FIG. 12 and elsewhere refers to the relative quantity of the fragrance ingredient in the fragrance composition by weight or volume or by parts. Here, the percentage of the fragrance ingredient coumarine is 42.78% and the percentage of the fragrance ingredient citronellol is 57.22%, indicating that a smaller amount of coumarine than citronellol is required to make the same olfactive contribution.

FIG. 12 also depicts a set of 7 icons to the left of the screen above the selection menu, which provide different options for display of the selection menu. For instance, these icons can be used to change between an olfactive contribution view (selected), a quantity view (top icon), a linking function described below, and a tableau or graphical view, as well as undo and re-do functionality. The olfactive contribution view may be toggled between an absolute view and a relative view of the olfactive contribution.

Calculation of the Display Size of Selected Fragrance Ingredient Pictograms

The display may be switched according to user input (for example using "buttons" on the edge of a touch screen) between the olfactive contribution representation and a quantity representation/mode. The olfactive contribution representation (also referred to as the odor value or OV representation/mode due to its close link to odor value) can be in linear or non-linear format. This non-linear format can allow easier understanding of compositions in which some pictograms are many factors bigger than others.

Equations for the radius (in pixels) of a circular pictogram in the different representations are as follows:

Quantity Visualisation:

$$r = \sqrt{q \times scaleCoef} * \text{base Radius}$$

Linear OV Visualisation:

$$r = OVI \times scaleCoef \times baseRadius \times OVIRadiusScale$$

Non-linear OV Visualisation:

$$r = \sqrt{OVI \times scaleCoef} \times \log baseRadius$$

There are 2 common variables in the calculations for both OV and quantity visualization.

$$scaleCoef \in [2; +\infty]$$

The scale coefficient is a dimensionless variable of between 2 and positive infinity and is a scaling variable which may be adjusted, for example using + and − buttons on the screen, situated for example in the olfactory design space.

$$baseRadius = dimensionX \times 0.03 \text{ and } \in [10; 70]$$

The basic radius is a variable with pixel units and is deduced from the dimension X in pixels of the screen multiplied by 0.03. The variable is between 10 and 70.

For the calculation of linear OV, the constant OVIRadiusScale is equal to 1/1000 and used to avoid oversizing of the pictograms.

For OV visualisation, the OVI (Odor Value Index) acts as the olfactive contribution and visually represents the contribution of a fragrance ingredient into a fragrance composition:

$$OVI = q \times OV$$

in which q is the quantity in absolute terms or in terms of concentration (the quantity of the fragrance ingredient as a ratio of the ingredient to the full composition either by volume or weight or by moles or molecules or any other suitable measure) and OV the Odor Value of the fragrance ingredient in question (and thus a constant).

FIG. 13 shows a more complex GUI display, allowing simultaneous display of two fragrance compositions, one above the other. In a first olfactive space for each fragrance composition, shown to the left, the fragrance ingredients are grouped into vapor pressure "slices": groups 1 to 8. These slices are presented in order along the y-axis as before. The x-axis represents olfactive contribution in the form of log (odor value* concentration). In a second olfactive space for each fragrance composition, shown to the right, the ingredients are shown as circles in a two-dimensional olfactive space, with the x-axis indicating the odor threshold and the y-axis indicating the vapor pressure of the fragrance ingredients. The olfactive contribution of the fragrance ingredients may be indicated by the size of the circles, but that is not shown here, and the circles are all of the same size. Of course, a different olfactive space may be used. For example, the spreadsheet shown in FIGS. 14a and 14b may replace the olfactive space shown to the right. Also, the user may switch between consecutive different olfactive spaces.

In any or all of these cases, a set of filters may be provided as shown to the right of the screen, so that the user can select what is displayed. Shown here, the user can filter by (from top to bottom) fragrance compositions, odor families, fragrance ingredients, concentration, VP slice and set thresholds for display of olfactive contribution. In this way, the user can focus on specific sub-data. For example, a perfumer may wish to balance by concentration. If there is a fragrance ingredient with a low concentration, the perfumer may wish to replace it with another fragrance ingredient at a higher concentration, to work in the middle linear range of the dose-response curve. Equally, a fragrance ingredient at a very high concentration may be replaced with an equivalent fragrance ingredient, to work in the preferred middle range. In both of these cases, the perfumer may filter by concentration to identify ingredients at undesirable concentrations.

To the left of the screen, there are buttons for the user to load a formula (fragrance composition) and carry out the calculation required for display, using KNIME in this case and select options for display, including selection of what the X-axis represents and how the coloring (shown here as shading) is used.

FIGS. 14a and 14b show a spreadsheet which can be viewed at the same terminal. The same filters as described in FIG. 13 are shown to the right of the screen. For each fragrance ingredient, the VP slice has been calculated (as shown in the column furthest to the left) and the spreadsheet also holds all the other data necessary for display in the olfactive spaces discussed above, including a code and fragrance ingredient name, concentration, vapor pressure, threshold, odor value, odor family, VP (100%), log (OC* concentration), log (OV)*concentration, OV*concentration and concentration.

Once the fragrance ingredients have been selected if necessary and the olfactive contribution values have been adjusted as desired, the user can initiate the preparation of the fragrance composition, e.g. by means of a sampling automat such as the one shown in FIG. 3. To this end, the olfactive contribution value of each selected fragrance ingredient is converted into a respective quantity of said fragrance ingredient to be used, based on a respective conversion factor.

The conversion factor of each fragrance ingredient is stored in an ingredient record pertaining to said fragrance ingredient. The conversion factors typically vary from fragrance ingredient to fragrance ingredient and are not necessarily linear over the whole olfactive contribution range.

As an example:

|  | Ingredient: | | |
| --- | --- | --- | --- |
|  | I1 | I2 | I3 |
| Target Olfactive Contribution Value: | 1 | 2 | 4 |
| Quantity Corresponding to Olfactive Contribution Value of 1000000: | 15 mg | 180 mg | 300 mg |
| Correlation: | linear | linear | polynomial |
| Amount to be Used in the Composition: | 15 mg | 360 mg | 2400 mg |

Hardware and Software Implementation

FIG. 15 is a schematic view of a simple software implementation of an embodiment using a spreadsheet program such as Excel, a calculator program such as KNIME and a visual program such as Spotfire. The skilled person is able to code dedicated programs/software that will perform data enrichment, calculation and/or visualization, preferably all in one. The program may run on a server via a browser or as a (potentially more fully functional) client. Conventional hardware may be provided, even in the form of a standalone terminal.

The spreadsheet is the current method of listing a fragrance composition, and the calculator enriches the data to add properties that are useful for a more intuitive display (any of odor threshold, vapor pressure, cLogP, odor family, stability parameters and the like). KNIME can also be programmed to group (slice or bin) the data for visualizations. Spotfire, or another display program, is used to provide the visualization.

FIG. 16 is a diagram of another, more complex, suitable application architecture. Here the client application runs inside a web browser (Windows) running HTML and JavaScript. The platform is used to create the application. A runtime environment is provided for communication between the application on one hand and a robot (Tecan™ Robot) and a read and write labelling device (NFC (Near Field Communication) Device) for the samples on the other hand. The runtime environment is a JavaScript environment labelled as Node.js and executes JavaScript code that controls communication with the robot and NFC device.

The client application uses a Websocket communication protocol to communicate with Node.js and Node.js uses a TCP (Transmission Control Protocol) socket to handle communication on a Local Area Network (LAN) between Node.js and the robot. The NFC Device, on the other hand, is linked to Node.js via a USB port.

Turning back to the client application, the web browser communicates securely with an application server using an SSL Websocket (Secure Socket Layer). The application server itself is a Tomcat 8™ and houses an orchestrator running in Java 8. This orchestrator is the central workflow management for the whole system and provides an authentication, permission control and CRUD (Create, Read and Update, Delete) operations over data. The orchestrator is in an environment with limited access and can only be accessed using SSL Websocket or SSH-Secure SHell (with RSA (Rivest-Shamir-Adleman) key only).

The server is connected to a database storing all the application data (including the ingredient database) via a Java Database Connectivity (JDBC) Application Programming Interface (API), which is an industry standard for connectivity between the Java programming language and a database. The database itself is hosted on the Neo4j server, which is a graph platform.

FIG. 17 is a conceptual diagram of a suitable server architecture. Within the intranet of a company, there are one or more client terminals (which may be at different physical locations). Client terminals may also be situated outside of the intranet. An identity provider in the intranet authenticates the client terminals via an SAML (Security Assertion Markup Language) request. Also in the intranet, Lab Service is a service for providing larger scale samples. The intranet is connected to a cloud service via a DMZ (demilitarized zone). The cloud includes two backends, one for the client functionality, and one for the orchestrator. They are connected together by a Json (JavaScript Object Notation) web socket. The clients and the identity provider communicate with the backend through the orchestrator. For example, the client uses a web socket/Json protocol with an SAML login request and the identity provider uses an Http request and SAML response, with the orchestrator generating a token for the client to authenticate.

When a user adds a fragrance ingredient to a formula, a new "component" is created by the application, and this component may be updated. This component is linked to a formula and to the fragrance ingredient that the user is adding or changing. With the technology used, all the data is persisted in the database (DB) in real time.

Summary

The present invention provides a method of predicting the temporal fragrance profile of a fragrance composition comprising a plurality of fragrance ingredients, the method comprising the steps of:
  determining the equilibrium headspace concentration of each fragrance ingredient;
  forming groups of fragrance ingredients having the same or a similar equilibrium headspace concentration;
  determining the olfactive contribution of each fragrance ingredient; and displaying the total olfactive contribution of each group of fragrance ingredients:
    wherein the total olfactive contributions of the groups are displayed in the order of their respective equilibrium headspace concentration to visualize the temporal fragrance profile of the fragrance composition.

The present invention also provides a method of adjusting the temporal fragrance profile of a fragrance composition comprising a plurality of fragrance ingredients.

Said method comprises the steps of:
    predicting the temporal fragrance profile of the fragrance composition according to the method described above;
    identifying at least one adjustable group of fragrance ingredients, the total olfactive contribution of which is too low or too high, respectively, relative to the total olfactive contributions of the other groups; and
    increasing or decreasing, respectively, the total olfactive contribution of the at least one adjustable group.

Clearly having visuals and plots helps the perfumer to better prepare his or her next trials.

In a particular embodiment, the total olfactive contribution of the at least one adjustable group is increased or decreased, respectively, by increasing or decreasing, respectively, the olfactive contribution of at least one fragrance ingredient present in the at least one adjustable group.

Alternatively or in addition, the total olfactive contribution of the at least one adjustable group may be increased or decreased, respectively, by adding at least one additional fragrance ingredient having an equilibrium headspace concentration corresponding to said at least one adjustable group or by removing at least one fragrance ingredient present in the at least one adjustable group, respectively.

The perfumer may choose to adjust the olfactive contribution of only a few or even only one fragrance ingredient. But it is also possible that the olfactive contributions of all the fragrance ingredients within one group are increased or decreased.

An experienced perfumer will typically know which of the fragrance ingredients within a group will provide the desired olfactive effect. Alternatively, if the method of the present invention is conducted on a computing system with a database containing information on the fragrance ingredients, the user may obtain certain information from the database.

The invention claimed is:

1. A computer-implemented method of predicting a temporal profile of at least one composition comprising a plurality of fragrance ingredients which are able to provide a fragrance, odor, or smell, the computer-implemented method using a processor to:
    retrieve a diffusion measure of how fast each fragrance ingredient diffuses into a headspace;
    form groups of fragrance ingredients having a similar diffusion measure;
    determine an olfactive contribution of each fragrance ingredient, the olfactive contribution comprising a perceived intensity of each fragrance ingredient at a distance from a source;
    calculate a total olfactive contribution of a group of fragrance ingredients using olfactive contributions of all fragrance ingredients forming the group; and
    providing a virtual olfactive fingerprint of the at least one composition based on total olfactive contributions of the groups of fragrance ingredients and diffusion measures of the groups of fragrance ingredients.

2. The computer-implemented method of claim 1, further comprising:
    visually depicting or visualizing the virtual olfactive fingerprint of the at least one composition.

3. The computer-implemented method of claim 1, further comprising:
    displaying the total olfactive contributions of the groups of fragrance ingredients in an order that is based on the diffusion measures of the groups of fragrance ingredients.

4. The computer-implemented method of claim 1, wherein the diffusion measure of how fast each fragrance ingredient diffuses into the headspace is an equilibrium headspace concentration, a partial vapor pressure or vapor pressure, a retention time on a gas chromatograph, or a vapor liquid equilibrium, or is based on a maximal abundance time where abundance in the headspace reaches a maximum.

5. The computer-implemented method of claim 1, wherein a graphical user interface displays the total olfactive contributions of the groups of fragrance ingredients in an olfactive space defined by an array of coordinates, each coordinate indicating a specific property of the plurality of fragrance ingredients, and wherein a first coordinate indicates the diffusion measure and a second coordinate indicates the olfactive contribution.

6. The computer-implemented method of claim 5, wherein the olfactive space provides a bar chart, wherein one bar is displayed per group of fragrance ingredients, with a length that represents the total olfactive contribution.

7. The computer-implemented method of claim 6, wherein each bar is divided into sections representing individual fragrance ingredients within the group.

8. The computer-implemented method of claim 1, wherein a graphical user interface displays the at least one composition as circles in a further two-dimensional olfactive space, with an x-axis indicating an odor threshold and a y-axis indicating the diffusion measure of each individual fragrance ingredient.

9. The computer-implemented method of claim 1, wherein a graphical user interface displays the at least one composition as user-positioned circles in a further two-dimensional olfactive space, and wherein the olfactive contribution of the fragrance ingredient is indicated by a size of the user-positioned circles.

10. The computer-implemented method of claim 1, wherein a graphical user interface displays one or more fields in which a user may select one or more fragrance compositions, the plurality of fragrance ingredients, odor families, the groups, or other aspect for display, or apply one or more thresholds to a concentration range or diffusion measures range for display.

11. The computer-implemented method of claim 1, further comprising:
    preparing the at least one composition.

12. The computer-implemented method of claim 1, further comprising:
    adjusting the plurality of fragrance ingredients of the at least one composition via a graphical user interface while visually observing an effect on the virtual olfactive fingerprint of the at least one composition.

13. The computer-implemented method of claim 1, further comprising:
    identifying or balancing unbalanced groups of the groups of fragrance ingredients based on the virtual olfactive fingerprint.

14. The computer-implemented method of claim 1, further comprising:
creating a virtual fragrance composition based on the virtual olfactive fingerprint via a graphical user interface.

15. The computer-implemented method of claim 14, further comprising:
harmonizing, boosting, enhancing, or balancing a fragrance profile of the at least one composition via the virtual fragrance composition and the graphical user interface.

16. The computer-implemented method of claim 1, wherein each fragrance ingredient is represented by a fragrance ingredient name.

17. The computer-implemented method of claim 1, wherein the at least one composition is retrieved from a database, and any changes to the at least one composition are stored back into the database.

18. The computer-implemented method of claim 1, wherein the diffusion measure is equilibrium headspace concentration or vapor pressure, and equilibrium headspace concentrations or vapor pressures of the plurality of fragrance ingredients of each group are within one order of magnitude.

19. The computer-implemented method of claim 1, further comprising:
displaying odor families of the plurality of fragrance ingredients.

20. The computer-implemented method of claim 19, further comprising: color coding the odor families of the plurality of fragrance ingredients.

21. The computer-implemented method of claim 1, wherein at least one group of the groups of fragrance ingredients consists of a single fragrance ingredient.

22. The computer-implemented method of claim 1, further comprising:
the processor converting, for each fragrance ingredient, the olfactive contribution to a corresponding quantity; and
dispensing and mixing the plurality of fragrance ingredients to provide the at least one composition.

23. The computer-implemented method of claim 22, wherein the at least one composition is obtained by the computer-implemented method of claim 22.

24. The computer-implemented method of claim 1, wherein the at least one composition is a fragrance composition.

25. The computer-implemented method of claim 1, wherein the at least one composition is a flavor composition.

26. The computer-implemented method of claim 1, wherein the at least one composition comprises a fragrance composition and a flavor composition.

27. The computer-implemented method of claim 26, wherein at least one group of the groups of fragrance ingredients consists of a single fragrance ingredient.

28. The computer-implemented method of claim 1, wherein the plurality of fragrance ingredients comprise a perfume chemical and a flavor chemical.

29. A non-transitory computer program which, when loaded onto at least one computer apparatus, configures the at least one computer apparatus to carry out the computer-implemented method of claim 1.

30. A method of adjusting the temporal profile of the at least one composition comprising the plurality of fragrance ingredients, the method comprising predicting the temporal profile of the at least one composition according to the computer-implemented method of claim 1; and
a graphical user interface (GUI) accepting user input from a user input means to change the total olfactive contribution of the group or the olfactive contribution of the fragrance ingredient, or to delete or add the fragrance ingredient, and the GUI changing a display accordingly.

31. The method of claim 30, wherein the total olfactive contribution of at least one adjustable group is increased or decreased, respectively, by adding at least one additional fragrance ingredient having the diffusion measure corresponding to the at least one adjustable group or by removing the at least one fragrance ingredient present in the at least one adjustable group, respectively.

32. The method of claim 30, wherein the user input is in a form of touch screen manipulation of the display or keyboard/mouse manipulation of the display, to change a representation of the group on the display.

33. A computer apparatus arranged to carry out a method of predicting a temporal profile of at least one composition comprising a plurality of fragrance ingredients which are able to provide a fragrance, odor, or smell, the computer apparatus comprising a processor to:
retrieve a diffusion measure of how fast each fragrance ingredient diffuses into a headspace;
form groups of fragrance ingredients having a similar diffusion measure;
determine an olfactive contribution of each fragrance ingredient, the olfactive contribution comprises a perceived intensity of each fragrance ingredient at a distance from a source;
calculate a total olfactive contribution of a group of fragrance ingredients as a sum of olfactive contributions of all fragrance ingredients forming the group; and
provide the temporal profile of the at least one composition based on total olfactive contributions of the groups of fragrance ingredients and diffusion measures of the groups of fragrance ingredients, wherein the temporal profile is defined between a first end and a second end opposite with respect to the first end, a first group of the groups diffuses into the headspace before one or more second groups of the groups diffuse into the headspace, the first group is disposed at or adjacent to the first end of the temporal profile, and the one or more second groups are disposed between the first group and the second end of the temporal profile.

34. The computer apparatus of claim 33, wherein the computer apparatus visually depicts or visualizes the temporal profile of the at least one composition.

35. The computer apparatus of claim 33, wherein at least one group of the groups of fragrance ingredients consists of a single fragrance ingredient.

36. The computer apparatus of claim 33, wherein the at least one composition is a fragrance composition.

37. The computer apparatus of claim 33, wherein the at least one composition is a flavor composition.

38. The computer apparatus of claim 33, wherein the at least one composition comprises a fragrance composition and a flavor composition.

39. The computer apparatus of claim 38, wherein at least one group of the groups of fragrance ingredients consists of a single fragrance ingredient.

40. The computer apparatus of claim 33, wherein the plurality of fragrance ingredients comprise a perfume chemical and a flavor chemical.

41. A computer-implemented method of predicting a temporal profile of at least one composition comprising a plurality of fragrance ingredients which are able to provide a fragrance, odor, or smell, the computer-implemented method using a processor to:
- determine an olfactive contribution of each fragrance ingredient, the olfactive contribution comprising a perceived intensity of each fragrance ingredient at a distance from a source; and
- form groups of fragrance ingredients having a similar olfactive contribution;
- retrieve an odor value for each fragrance ingredient, wherein the odor value is determined by dividing an equilibrium headspace concentration of the fragrance ingredient by an odor threshold of the fragrance ingredient;
- calculate a total olfactive contribution of a group of fragrance ingredients using olfactive contributions of all fragrance ingredients forming the group; and
- providing a virtual olfactive fingerprint of the at least one composition based on total olfactive contributions of the groups of fragrance ingredients and odor values of the groups of fragrance ingredients.

42. The computer-implemented method of claim 41, further comprising:
- visually depicting or visualizing the virtual olfactive fingerprint value of the at least one composition.

43. The computer-implemented method of claim 41, further comprising:
- displaying the total olfactive contributions of the groups of fragrance ingredients in an order that is based on the odor values of the groups of fragrance ingredients.

44. The computer-implemented method of claim 41, further comprising:
- preparing the at least one composition.

45. The computer-implemented method of claim 41, wherein at least one group of the groups of fragrance ingredients consists of a single fragrance ingredient.

46. The computer-implemented method of claim 41, wherein the at least one composition is a fragrance composition.

47. The computer-implemented method of claim 41, wherein the at least one composition is a flavor composition.

48. The computer-implemented method of claim 41, wherein the at least one composition comprises a fragrance composition and a flavor composition.

49. The computer-implemented method of claim 48, wherein at least one group of the groups of fragrance ingredients consists of a single fragrance ingredient.

50. The computer-implemented method of claim 41, wherein the plurality of fragrance ingredients comprise a perfume chemical and a flavor chemical.

* * * * *